US008853152B2

(12) United States Patent (10) Patent No.: US 8,853,152 B2
Bittorf et al. (45) Date of Patent: Oct. 7, 2014

(54) PHARMACEUTICAL COMPOSITIONS

(75) Inventors: Kevin Bittorf, Cambridge, MA (US); Jeffrey Kastra, South Boston, MA (US); Filipe Gaspar, Loures (PT)

(73) Assignee: Vertex Pharmaceuticals Incorporated, Boston, MA (US)

( * ) Notice: Subject to any disclaimer, the term of this patent is extended or adjusted under 35 U.S.C. 154(b) by 858 days.

(21) Appl. No.: 12/481,962

(22) Filed: Jun. 10, 2009

(65) Prior Publication Data

US 2009/0247468 A1 Oct. 1, 2009

Related U.S. Application Data

(63) Continuation of application No. 11/687,779, filed on Mar. 19, 2007, now abandoned.

(60) Provisional application No. 60/784,275, filed on Mar. 20, 2006, provisional application No. 60/871,692, filed on Dec. 22, 2006.

(51) Int. Cl.
*A61K 31/00* (2006.01)

(52) U.S. Cl.
USPC .......................................................... 514/4.8

(58) Field of Classification Search
None
See application file for complete search history.

(56) References Cited

U.S. PATENT DOCUMENTS

| 6,308,434 | B1 | 10/2001 | Chickering, III |
| 6,548,555 | B1 | 4/2003 | Curatolo |
| 6,919,423 | B2 | 7/2005 | Llinas-Brunet |

FOREIGN PATENT DOCUMENTS

| WO | 0168092 | A2 | 9/2001 |
| WO | 0218369 | A2 | 3/2002 |
| WO | 03063822 | A2 | 8/2003 |

OTHER PUBLICATIONS

Alder, Pharm. Res., 17 (2000), pp. 863-870.
Quaglia, J. Control Release, 86 (2003), pp. 267-278.
Zambaux, J. Control Release, 60 (1999), pp. 179-188.

*Primary Examiner* — Craig Ricci
(74) *Attorney, Agent, or Firm* — Honigman Miller Schwartz & Cohn LLP; Noel E. Day; Jonathan P. O'Brien

(57) ABSTRACT

Methods of spray drying are described.

7 Claims, 5 Drawing Sheets

FIG. 3

| Outlet Temperature °C | Feed Pressure bar | Cyclone Pressure cmH2O | Condenser Setpoint Temp °C | SS SK-MFP Nozzle | Solids Loading wt% | PS microns | span | bulk density g/cc | tap density g/cc | LOD % | Solution Feedrate kg/hr | KF %w/w | DCM ppm | Acetone ppm |
|---|---|---|---|---|---|---|---|---|---|---|---|---|---|---|
| 30 | 40 | 12 | -3 | 50/21 | 17 | 106.2 | 1.52 | 0.4 | 0.5 | 10.03 | 183 | 0.63 | 108628 | 29701 |
| 50 | 20 | 12 | -3 | 50/21 | 17 | 80.88 | 1.98 | 0.23 | 0.27 | 7.02 | 130 | 1.36 | 59090 | 21140 |
| 50 | 40 | 12 | -3 | 54/21 | 17 | 58.96 | 1.96 | 0.22 | 0.28 | 6.28 | 142 | 0.63 | 49452 | 14469 |
| 30 | 20 | 12 | -3 | 54/21 | 17 | 93.84 | 1.87 | 0.35 | 0.45 | 10.27 | 103 | 1.04 | 45626 | 11640 |
| 40 | 30 | 12 | -3 | 54/21 | 17 | 75.5 | 1.86 | 0.31 | 0.38 | 8.1 | 124 | 0.67 | 60395 | 16483 |
| 30 | 30 | 12 | -3 | 54/21 | 17 | 78.75 | 1.72 | 0.3 | 0.38 | 8.68 | 124 | 0.63 | 68464 | 21373 |
| 30 | 30 | 12 | -3 | 54/21 | 12 | 66.71 | 1.74 | 0.33 | 0.43 | 7.26 | 124 | 0.74 | 55802 | 127 |
| 30 | 30 | 12 | -3 | 54/21 | 12 | 63.09 | 1.8 | 0.34 | 0.44 | 8.09 | 124 | 0.74 | 54704 | 14323 |
| 50 | 20 | 12 | -3 | 54/21 | 12 | 64.98 | 1.84 | 0.25 | 0.32 | 6.59 | 99 | 0.55 | 23645 | 7310 |
| 30 | 40 | 12 | -3 | 54/21 | 12 | 66.51 | 1.71 | 0.39 | 0.51 | 9.89 | 142 | 0.85 | 42078 | 9485 |
| 30 | 20 | 12 | -3 | 50/21 | 12 | 86.71 | 2.06 | 0.4 | 0.53 | 11.3 | 183 | 0.63 | 80579 | 19275 |
| 50 | 40 | 12 | -3 | 50/21 | 12 | 52.8 | 2.11 | 0.25 | 0.32 | 6.42 | 185 | 0.63 | 20805 | 6340 |
| 30 | 30 | 12 | -3 | 54/21 | 17 | 95.53 | 1.59 | 0.35 | 0.46 | 10.41 | 103 |  | 99084 | 28431 |
| 30 | 40 | 12 | -10 | 52/21 | 15 | 95.26 | 1.45 | 0.34 | 0.45 | 8.96 | 160 | 0.71 | 52975 | 24399 |
| 40 | 30 | 12 | -10 | 52/21 | 15 | 89.89 | 1.71 | 0.28 | 0.36 | 7.01 | 137 | 0.6 | 41192 | 21435 |
| 40 | 30 | 12 | -10 | 52/21 | 13 | 114.29 | 1.5 | 0.33 | 0.41 | 10.51 | 136 | 0.57 | 55576 | 31638 |
| 40 | 40 | 12 | -10 | 52/21 | 13 | 94.09 | 1.68 | 0.27 | 0.34 | 8.2 | 155 | 0.43 | 41051 | 26826 |
| 30 | 50 | 12 | -10 | 54/21 | 15 | 71.81 | 1.56 | 0.34 | 0.47 | 8.32 | 155 |  | 43413 | 13946 |
| 30 | 30 | 12 | -10 | 54/21 | 15 | 83.31 | 1.55 | 0.34 | 0.44 | 6.98 | 123 |  | 60819 | 21951 |
| 26 | 50 | 12 | -10 | 54/21 | 15 | 68.75 | 1.63 | 0.37 |  | 10.02 | 155 |  | 53482 | 16955 |
| 26 | 40 | 12 | -10 | 52/21 | 15 | 86.91 | 1.52 | 0.4 | 0.54 | 10.78 | 122 |  | 79148 | 27092 |
| 28 | 30 | 12 | -10 | 54/21 | 15 | 75.17 | 1.65 | 0.37 | 0.48 | 8.67 | 141 |  | 43413 | 13946 |
| 28 | 40 | 10 | -10 | 52/21 | 20 | 110.61 | 1.87 | 0.27 | 0.33 | 8.7 | 132 |  | 69673 | 21067 |
| 40 | 25 | 10 | -10 | 52/21 | 20 | 93.05 | 1.91 | 0.25 | 0.31 | 7.96 | 180 |  |  |  |
| 40 | 50 |  |  |  |  |  |  |  |  |  |  |  |  |  |

FIG. 3 (Continued)

| | | | | | | | | | | | | |
|---|---|---|---|---|---|---|---|---|---|---|---|---|
| 30 | 50 | 10 | -10 | 52/21 | 20 | 102.8 | 1.74 | 0.33 | 0.42 | 7.43 | 184 | . | . |
| 30 | 25 | 10 | -10 | 52/21 | 20 | 146.58 | 1.86 | 0.33 | 0.41 | 9.6 | 133 | . | . |
| 27 | 70 | 10 | -10 | 56/21 | 20 | 78.18 | 1.69 | 0.35 | 0.46 | 8.6 | 150 | 80368 | 10511 |
| 40 | 25 | 10 | -10 | 52/21 | 17 | 102.27 | 1.71 | 0.26 | 0.31 | 8.93 | 130 | . | . |
| 40 | 50 | 10 | -10 | 52/21 | 17 | 85.48 | 1.75 | 0.27 | 0.35 | 9.22 | 184 | . | . |
| 30 | 50 | 10 | -10 | 52/21 | 17 | 104.95 | 1.51 | 0.31 | 0.41 | 11.4 | 185 | . | . |
| 30 | 25 | 10 | -10 | 52/21 | 17 | 111.22 | 1.71 | 0.31 | 0.4 | 10.38 | 131 | . | . |
| 27 | 60 | 10 | -10 | 54/21 | 17 | 86.14 | 1.68 | 0.33 | 0.47 | 10.63 | 170 | 75835 | 31366 |
| 40 | 25 | 10 | -10 | 52/21 | 15 | 79.57 | 1.77 | 0.26 | 0.33 | 9.41 | 130 | . | . |
| 40 | 50 | 10 | -10 | 52/21 | 15 | 67.06 | 1.79 | 0.26 | 0.34 | 5.94 | 183 | . | . |
| 30 | 50 | 10 | -10 | 52/21 | 15 | 84.18 | 1.56 | 0.31 | 0.43 | 10.36 | 183 | . | . |
| 30 | 25 | 10 | -10 | 52/21 | 15 | 96.86 | 1.62 | 0.31 | 0.4 | 10.98 | 130 | . | . |
| 23 | 60 | 10 | -10 | 54/21 | 15 | 110.61 | 1.87 | 0.27 | 0.48 | 8.7 | 132 | 69444 | 27689 |
| 23 | 65 | 10 | -10 | 54/21 | 17 | 93.62 | 1.34 | 0.34 | 0.45 | 8.5 | 178 | . | . |
| 23 | 65 | 10 | -3 | 54/21 | 17 | 93.42 | 1.4 | 0.4 | 0.5 | 10.38 | 178 | . | . |
| 22 | 65 | 10 | -10 | 56/21 | 17 | 63.52 | 1.56 | 0.36 | 0.49 | 6.96 | 146 | . | . |
| 22 | 65 | 10 | -3 | 56/21 | 17 | 50.81 | 1.85 | 0.39 | 0.54 | 8.81 | 146 | . | . |

PHARMACEUTICAL COMPOSITIONS

CROSS-REFERENCE TO RELATED APPLICATIONS

This application is a continuation application of U.S. patent application Ser. No. 11/687,779, filed on Mar. 19, 2007, which in turn claims the benefit of U.S. Provisional Application No. 60/784,275, filed on Mar. 20, 2006 and U.S. Provisional Application No. 60/871,692, filed on Dec. 22, 2006; the entire teachings of which are incorporated herein by reference.

TECHNICAL FIELD

This invention relates to pharmaceutical compositions and methods of making the same.

BACKGROUND

It is known in the pharmaceutical arts that low-solubility drugs often show poor bioavailability or irregular absorption, the degree of irregularity being affected by factors such as dose level, fed state of the patient, and form of the drug.

Solid dispersions of a drug in a matrix can be prepared by forming a homogeneous solution or melt of the drug and matrix material followed by solidifying the mixture by cooling or removal of solvent. Such solid dispersions of drugs often show enhanced bioavailability when administered orally relative to oral compositions comprising undispersed drug.

Spray drying is the most widely used industrial process involving particle formation and drying and can be used to produce solid dispersions of drug compounds. It is highly suited for the continuous production of dry solids in either powder, granulate or agglomerate form from liquid feedstocks as solutions, emulsions and pumpable suspensions. Therefore, spray drying is an ideal process where the end-product must comply to precise quality standards regarding particle size distribution, residual moisture content, bulk density, and particle shape.

Spray drying generally involves the atomization of a liquid feedstock into a spray of droplets and contacting the droplets with hot air or gas in a drying chamber. The sprays are generally produced by either rotary (wheel) or nozzle atomizers. Evaporation of moisture from the droplets and formation of dry particles proceed under controlled temperature and airflow conditions.

SUMMARY

The inventors have discovered that varying the solvent, for example including a non-volatile or high boiling solvent, during spray drying of a drug (e.g., VX-950) or other therapeutic agent (e.g., a solid dispersion of the drug or therapeutic agent) can improve the properties of the resulting product (e.g., a solid dispersion such as an amorphous solid dispersion of the drug or therapeutic agent). In some instances, including a non-volatile or high boiling solvent as a component of a solvent mixture in the spray drying process can result in an increase in the amount of time required for the resulting particles to solidify and/or dry, thereby in some instances providing improved particles, e.g., particles that are larger and/or denser and/or more flowable than the same particles had they been obtained using a solvent system without a non-volatile or high boiling solvent. In some instances, including a non-volatile or high boiling solvent as a component of a solvent mixture in the spray drying process can help solubilize a component (e.g., a surfactant or polymer) that is present in the feed solution (e.g., the solution or suspension being spray dried). Spray drying to generate a solid dispersion can be performed, e.g., on a homogeneous solution, melt, or suspension of the drug and matrix material followed by solidifying the mixture by cooling or removal of solvent.

In one aspect, the method includes a method of spray drying a drug (e.g., VX-950) or other therapeutic agent, the method comprising forming a mixture of the drug in a suitable solvent or combination of solvents where at least one solvent is a non-volatile or high boiling solvent to form a mixture of the drug and solvent, and then spray-drying the mixture to obtain amorphous drug product. The resulting drug product can, for example, have a bulk density of about 0.25 to about 0.50, e.g., about 0.35 to about 0.45, e.g., about 0.37 or about 0.41. The resulting drug product can, for example, have a d50 of about 35 to about 55, e.g., about 40 to about 50, e.g., about 43 or about 47. The mixture can be either a solution or a suspension.

In some embodiments, the method includes a method of spray drying a drug (e.g., VX-950) or other therapeutic agent, the method comprising forming a mixture of the drug in a suitable solvent or combination of solvents where at least one solvent is a non-volatile or high boiling solvent to form a mixture of the drug and solvent, and then spray-drying the mixture to obtain amorphous drug product, with the proviso that the drug is other than N-[2,4-bis(1,1-dimethylethyl)-5-hydroxyphenyl]-1,4-dihydro-4-oxoquinoline-3-carboxamide.

In some embodiments, the drug is a small molecule drug, for example a drug having a molecular weight of less than about 1000 daltons, e.g., less than about 750 daltons or less than about 500 daltons.

In some embodiments, the drug is a poorly soluble drug.

The drug can be selected from one of the following classifications: analgesics, anti-inflammatory agents, antihelminthics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, β-blockers, cardiac inotropic agents, corticosteroids, diuretics, anti-parkinsonian agents, gastro-intestinal agents, histamine receptor antagonists, keratolyptics, lipid regulating agents, anti-anginal agents, Cox-2 inhibitors, leukotriene inhibitors, macrolides, muscle relaxants, nutritional agents, opiod analgesics, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, or non-essential fatty acids.

In some preferred embodiments, the drug is an anti-viral agent, for example an antiviral agent used to treat Hepatitis C (HepC), such as a HepC protease inhibitor. In some most preferred embodiments, the drug is VX-950:

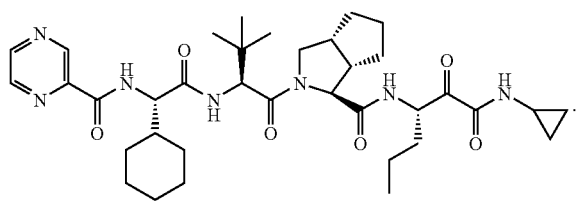

VX-950

In some embodiments, the solvent is a combination of solvent components including at least one non-volatile solvent. For example, the solvent is a combination of components that includes both a volatile solvent and a non-volatile solvent.

Examples of suitable volatile solvents include those that dissolve or suspend the drug either alone or in combination with another co-solvent. In some preferred examples, the solvent or solvent combination completely dissolves the drug.

Examples of volatile solvents include methylene chloride, acetone, chloroform, and THF. Examples of non-volatile solvents include organic acids such as glacial acetic acid, DMSO, DMF, and water.

In some embodiments, the non-volatile solvent is a component in a solvent system. For example the non-volatile solvent is present as a component in a solvent from about 0.1% to about 20% by wt (e.g., from about 0.5% to about 3%, from about 1% to about 5%, from about 3% to about 15%, from about 4% to about 12%, or from about 5% to about 10%).

In some preferred embodiments, the solvent system is a combination of a volatile solvent or combination of solvents such as methylene chloride and acetone with a non-volatile solvent such as glacial acetic acid. For example, the solvent system comprises from about 40% to about 80% methylene chloride, from about 20% to about 35% acetone, and from about 0.1% to about 15% glacial acetic acid (e.g., from about 50% to about 70% methylene chloride, from about 25% to about 30% acetone, and from about 3% to about 12% glacial acetic acid).

In some embodiments, the solvent system comprises glacial acetic acid.

In some embodiments, the solvent system comprises a combination of glacial acetic acid with at least one volatile solvent such as acetone and/or methylene chloride (e.g., a mixture of methylene chloride and acetone).

In some embodiments, the mixture also includes a surfactant, for example, sodium lauryl sulfate (SLS) or Vitamin E or a derivative thereof (e.g., Vitamin E TPGS).

In some preferred embodiments, the solvent system is a combination of a volatile solvent or combination of solvents such as methylene chloride and acetone with a non-volatile solvent such as water. For example, the solvent system comprises from about 40% to about 80% methylene chloride, from about 20% to about 35% acetone, and from about 0.1% to about 15% water (e.g., from about 50% to about 70% methylene chloride, from about 25% to about 30% acetone, and from about 1% to about 5% water).

In some embodiments, the solvent system comprises water.

In some embodiments, the solvent system comprises a combination of water with at least one volatile solvent such as acetone and/or methylene chloride (e.g., a mixture of methylene chloride and acetone).

In some embodiments, the mixture also includes a surfactant, for example, sodium lauryl sulfate (SLS) or Vitamin E or a derivative thereof (e.g., Vitamin E TPGS).

In another aspect, the method of spray drying includes forming a solid dispersion of a drug (e.g., VX-950) and one or more polymers comprising forming or providing a mixture of the drug and the polymer(s) in a suitable solvent or combination of solvents where at least one solvent is a non-volatile or high boiling solvent to form a mixture of the drug, polymer(s) and solvent, and then spray-drying the mixture to obtain a solid dispersion drug product. The resulting drug product can, for example, have a bulk density of about 0.25 to about 0.50, e.g., about 0.35 to about 0.45, e.g., about 0.37 or about 0.41. The resulting drug product can, for example, have a d50 of about 35 to about 55, e.g., about 40 to about 50, e.g., about 43 or about 47. The mixture can be either a solution or a suspension. In a preferred embodiment, the solid dispersion product is an amorphous solid dispersion. For example, an amorphous solid dispersion that is substantially free of crystalline drug product.

Examples of polymers for the solid dispersion include one or more water-soluble polymer(s) or partially water-soluble polymer(s). Water-soluble or partially water-soluble polymers include but are not limited to, cellulose derivatives (e.g., hydroxypropylmethylcellulose (HPMC; also known as hypromellose), hydroxypropylcellulose (HPC)) or ethylcellulose; polyvinylpyrrolidones (PVP); polyethylene glycols (PEG); polyvinyl alcohols (PVA); acrylates, such as polymethacrylate (e.g., Eudragit® E); cyclodextrins (e.g., β-cyclodextin) and copolymers and derivatives thereof, including for example PVP-VA (polyvinylpyrollidone-vinyl acetate).

In some preferred embodiments, the polymer is hydroxypropylmethylcellulose (HPMC), such as HMPC60SH50, HPMC E50 or HPMCE15.

In some embodiments, the polymer is a pH-dependent enteric polymer. Such pH-dependent enteric polymers include, but are not limited to, cellulose derivatives (e.g., cellulose acetate phthalate (CAP)), hydroxypropyl methyl cellulose phthalates (HPMCP), hydroxypropyl methyl cellulose acetate succinate (HPMCAS; also known as hypromellose acetate succinate), carboxymethylcellulose (CMC) or a salt thereof (e.g., a sodium salt such as (CMC-Na)); cellulose acetate trimellitate (CAT), hydroxypropylcellulose acetate phthalate (HPCAP), hydroxypropylmethyl-cellulose acetate phthalate (HPMCAP), and methylcellulose acetate phthalate (MCAP), or polymethacrylates (e.g., Eudragit® S).

In some preferred embodiments, the polymer is hydroxypropyl methyl cellulose acetate succinate (HPMCAS), e.g., HMPC AS-HG.

In another embodiment, the polymer(s) is an insoluble cross-linked polymer, for example a polyvinylpyrrolidone (e.g., Crospovidone).

In another embodiment, the polymer(s) is polyvinylpyrrolidone (PVP).

In some embodiments, the polymer is a mixture of two or more polymers (e.g., a combination of two cellulosic polymers such as HPMC and HPMCAS).

In some embodiments, the polymer(s) is present in an amount of from about 30% to about 70% by weight in the solid dispersion.

In some embodiments the drug is a small molecule drug, for example a drug having a molecular weight of less than about 1000 daltons, e.g., less than about 750 daltons or less than about 500 daltons.

In some embodiments, the drug is a poorly soluble drug.

The drug can be selected from one of the following classifications: analgesics, anti-inflammatory agents, antihelminthics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, β-blockers, cardiac inotropic agents, corticosteroids, diuretics, anti-parkinsonian agents, gastro-intestinal agents, histamine receptor antagonists, keratolyptics, lipid regulating agents, anti-anginal agents, Cox-2 inhibitors, leukotriene inhibitors, macrolides, muscle relaxants, nutritional agents, opiod analgesics, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, or non-essential fatty acids.

In some preferred embodiments, the drug is an anti-viral agent, for example an antiviral agent used to treat HepC, such as a HepC protease inhibitor. In some most preferred embodiments, the drug is VX-950:

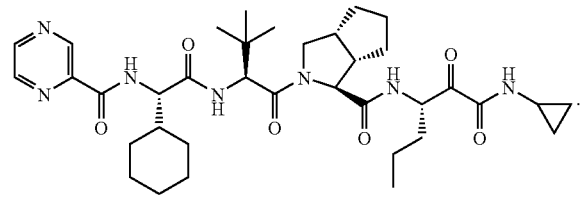

VX-950

In some embodiments, the solvent is a combination of solvent components including at least one non-volatile solvent. For example, the solvent is a combination of components that includes both a volatile solvent and a non-volatile solvent.

Examples of suitable volatile solvents include those that dissolve or suspend the drug either alone or in combination with another co-solvent. In some preferred examples, the solvent or solvent combination completely dissolves the drug.

Examples of volatile solvents include methylene chloride, acetone, chloroform, and THF. Examples of non-volatile solvents include organic acids such as glacial acetic acid, DMSO, DMF, and water.

In some embodiments, the non-volatile solvent is a component in a solvent system. For example the non-volatile solvent is present as a component in a solvent from about 0.1% to about 20% by wt (e.g., from about 0.5% to about 3%, from about 1% to about 5%, from about 3% to about 15%, from about 4% to about 12%, or from about 5% to about 10%).

In some preferred embodiments, the solvent system is a combination of a volatile solvent or combination of solvents such as methylene chloride and acetone with a non volatile solvent such as glacial acetic acid. For example, the solvent system comprises from about 40% to about 80% methylene chloride, from about 20% to about 35% acetone, and from about 0.1% to about 15% glacial acetic acid (e.g., from about 50% to about 70% methylene chloride, from about 25% to about 30% acetone, and from about 3% to about 12% glacial acetic acid).

In some embodiments, the mixture also includes a surfactant, for example, sodium lauryl sulfate (SLS) or Vitamin E or a derivative thereof (e.g., Vitamin E TPGS).

In some preferred embodiments, the solvent system is a combination of a volatile solvent or combination of solvents such as methylene chloride and acetone with a non volatile solvent such as water. For example, the solvent system comprises from about 40% to about 80% methylene chloride, from about 20% to about 35% acetone, and from about 0.1% to about 15% water (e.g., from about 50% to about 70% methylene chloride, from about 25% to about 30% acetone, and from about 1% to about 5% water).

In some embodiments, the mixture also includes a surfactant, for example, sodium lauryl sulfate (SLS) or Vitamin E or a derivative thereof (e.g., Vitamin E TPGS).

In another aspect, the process includes
a) forming or providing a mixture of a poorly water soluble drug (e.g., VX-950), at least one polymer, and a solvent system comprising at least one non-volatile solvent; and
b) spray-drying the mixture to form a solid dispersion comprising a poorly water soluble drug to obtain a solid dispersion of the drug.

The resulting dispersion can, for example, have a bulk density of about 0.25 to about 0.50, e.g., about 0.35 to about 0.45, e.g., about 0.37 or about 0.41. The resulting dispersion can, for example, have a d50 of about 35 to about 55, e.g., about 40 to about 50, e.g., about 43 or about 47.

In some embodiments the drug is a small molecule drug, for example a drug having a molecular weight of less than about 1000 daltons, e.g., less than about 750 daltons or less than about 500 daltons.

The drug can be selected from one of the following classifications: analgesics, anti-inflammatory agents, antihelminthics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, β-blockers, cardiac inotropic agents, corticosteroids, diuretics, anti-parkinsonian agents, gastro-intestinal agents, histamine receptor antagonists, keratolyptics, lipid regulating agents, anti-anginal agents, Cox-2 inhibitors, leukotriene inhibitors, macrolides, muscle relaxants, nutritional agents, opiod analgesics, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, or non-essential fatty acids.

In some preferred embodiments, the drug is an anti-viral agent, for example an antiviral agent used to treat HepC, such as a HepC protease inhibitor. In some most preferred embodiments, the drug is VX-950:

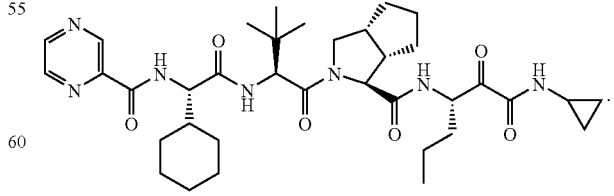

VX-950

In some embodiments, the solvent is a combination of solvents including at least one non-volatile solvent. For example, the solvent is a combination of components that includes both a volatile solvent and a non-volatile solvent.

Examples of suitable volatile solvents include those that dissolve or suspend the drug either alone or in combination with another co-solvent. In some preferred examples, the solvent or solvent combination completely dissolves the drug.

Examples of volatile solvents include methylene chloride, acetone, chloroform, THF.

Examples of non-volatile solvents include organic acids such as glacial acetic acid, DMSO, DMF, and water.

In some embodiments, the non-volatile solvent is a component in a solvent system. For example the non-volatile solvent is present as a component in a solvent from about 0.1% to about 20% by wt (e.g., from about 0.5% to about 3%, from about 1% to about 5%, from about 3% to about 15%, from about 4% to about 12%, or from about 5% to about 10%).

In some preferred embodiments, the solvent system is a combination of a volatile solvent or combination of solvents such as methylene chloride and acetone with a non volatile solvent such as glacial acetic acid. For example, the solvent system comprises from about 40% to about 80% methylene chloride, from about 20% to about 35% acetone, and from about 0.1% to about 15% glacial acetic acid (e.g., from about 50% to about 70% methylene chloride, from about 25% to about 30% acetone, and from about 3% to about 12% glacial acetic acid).

In some preferred embodiments, the solvent mixture comprises from about 40% to about 80% methylene chloride, from about 20% to about 35% acetone, and from about 0.1% to about 15% water (e.g., from about 50% to about 70% methylene chloride, from about 25% to about 30% acetone, and from about 1% to about 5% water).

In a preferred embodiment, the solvent mixture comprises a percent weight ratio of methylene chloride to acetone to non-volatile solvent is about 75:24:1.

In some embodiments, the mixture also includes a surfactant, for example, sodium lauryl sulfate (SLS) or Vitamin E or a derivative thereof (e.g., Vitamin E TPGS).

Examples of polymers for the solid dispersion include one or more water-soluble polymer(s) or partially water-soluble polymer(s). Water-soluble or partially water-soluble polymers include but are not limited to, cellulose derivatives (e.g., hydroxypropylmethylcellulose (HPMC), hydroxypropylcellulose (HPC)) or ethylcellulose; polyvinylpyrrolidones (PVP); polyethylene glycols (PEG); polyvinyl alcohols (PVA); acrylates, such as polymethacrylate (e.g., Eudragit® E); cyclodextrins (e.g., β-cyclodextin) and copolymers and derivatives thereof, including for example PVP-VA (polyvinylpyrollidone-vinyl acetate).

In some preferred embodiments, the polymer is hydroxypropylmethylcellulose (HPMC), such as HPMC60SH50, HPMC E50 or HPMCE15.

In some embodiments, the polymer is a pH-dependent enteric polymer. Such pH-dependent enteric polymers include, but are not limited to, cellulose derivatives (e.g., cellulose acetate phthalate (CAP)), hydroxypropyl methyl cellulose phthalates (HPMCP), hydroxypropyl methyl cellulose acetate succinate (HPMCAS), carboxymethylcellulose (CMC) or a salt thereof (e.g., a sodium salt such as (CMC-Na)); cellulose acetate trimellitate (CAT), hydroxypropylcellulose acetate phthalate (HPCAP), hydroxypropylmethylcellulose acetate phthalate (HPMCAP), and methylcellulose acetate phthalate (MCAP), or polymethacrylates (e.g., Eudragit® S).

In some preferred embodiments, the polymer is hydroxypropyl methyl cellulose acetate succinate (HPMCAS), e.g., HPMC AS-HG.

In another embodiment, the polymer(s) is an insoluble cross-linked polymer, for example a polyvinylpyrrolidone (e.g., Crospovidone).

In another embodiment, the polymer(s) is polyvinylpyrrolidone (PVP).

In some embodiments, the polymer is a mixture of two or more polymers (e.g., a combination of two cellulosic polymers such as HPMC and HPMCAS).

In some embodiments, the polymer(s) is present in an amount of from about 30% to about 90% by weight in the solid dispersion.

In some embodiments, the mixture also includes a surfactant, for example, sodium lauryl sulfate (SLS) or Vitamin E or a derivative thereof (e.g., Vitamin E TPGS).

In another aspect, this disclosure provides a process for preparing a solid dispersion of VX-950 comprising:

a) forming or providing a solution of VX-950, a cellulosic polymer, and a solvent, wherein the solvent comprises at least one non-volatile solvent component (e.g., glacial acetic acid);

b) spray-drying the mixture to form a solid amorphous dispersion comprising VX-950 and the cellulosic polymer.

The resulting diseprsion can, for example, have a bulk density of about 0.25 to about 0.50, e.g., about 0.35 to about 0.45, e.g., about 0.37 or about 0.41. The resulting dispersion can, for example, have a d50 of about 35 to about 55, e.g., about 40 to about 50, e.g., about 43 or about 47.

In some embodiments, the polymer is HPMC, HPMCAS, or a mixture thereof. In some preferred embodiments, the polymer is HPMCAS or a mixture of HPMC and HPMCAS.

Examples of suitable volatile solvents include those that dissolve or suspend the drug either alone or in combination with another co-solvent. In some preferred examples, the solvent or solvent combination completely dissolves the drug.

Examples of volatile solvents include methylene chloride, acetone, chloroform, THF.

Examples of non-volatile solvents include organic acids such as glacial acetic acid, DMSO, DMF, and water.

In some embodiments, the non-volatile solvent is a component in a solvent system. For example the non-volatile solvent is present as a component in a solvent from about 0.1% to about 20% by wt (e.g., from about 0.5% to about 3%, from about 1% to about 5%, from about 3% to about 15%, from about 4% to about 12%, or from about 5% to about 10%).

In some preferred embodiments, the solvent system is a combination of a volatile solvent or combination of solvents such as methylene chloride and acetone with a non volatile solvent such as glacial acetic acid or water. For example, the solvent system comprises from about 40% to about 80% methylene chloride, from about 20% to about 35% acetone, and from about 0.1% to about 15% glacial acetic acid (e.g., from about 50% to about 70% methylene chloride, from about 25% to about 30% acetone, and from about 3% to about 12% glacial acetic acid). For example, the solvent system comprises from about 40% to about 80% methylene chloride, from about 20% to about 35% acetone, and from about 0.1% to about 15% water (e.g., from about 50% to about 70% methylene chloride, from about 25% to about 30% acetone, and from about 1% to about 5% water).

In some embodiments, the mixture also includes a surfactant, for example, sodium lauryl sulfate (SLS) or Vitamin E or a derivative thereof (e.g., Vitamin E TPGS).

In some embodiments, the solvent comprises a mixture of methylene chloride, acetone, and glacial acetic acid.

In some embodiments, the solvent comprises a mixture of methylene chloride, acetone, and water.

In another aspect, this disclosure provides a process for preparing a solid dispersion of VX-950 comprising a) forming or providing a mixture of VX-950, at least one cellulosic polymer, and a solvent wherein the solvent comprises glacial acetic acid; and b) spray-drying the mixture to form a solid dispersion comprising VX-950.

The resulting dispersion can, for example, have a bulk density of about 0.25 to about 0.50, e.g., about 0.35 to about 0.45, e.g., about 0.37 or about 0.41. The resulting dispersion can, for example, have a d50 of about 35 to about 55, e.g., about 40 to about 50, e.g., about 43 or about 47.

In some embodiments, the polymer is HPMC, HPMCAS, or a mixture thereof. In some preferred embodiments, the polymer is HPMCAS or a mixture of HPMC and HPMCAS.

In another aspect, this disclosure provides a process for preparing a solid dispersion of VX-950 comprising a) forming or providing a mixture of VX-950, at least one cellulosic polymer, and a solvent wherein the solvent comprises water; and b) spray-drying the mixture to form a solid dispersion comprising VX-950.

The resulting dispersion can, for example, have a bulk density of about 0.25 to about 0.50, e.g., about 0.35 to about 0.45, e.g., about 0.37 or about 0.41. The resulting dispersion can, for example, have a d50 of about 35 to about 55, e.g., about 40 to about 50, e.g., about 43 or about 47.

In some embodiments, the polymer is HPMC, HPMCAS, or a mixture thereof. In some preferred embodiments, the polymer is HPMCAS or a mixture of HPMC and HPMCAS.

In some embodiments, the solvent also comprises a volatile solvent or combination of solvents that dissolve or suspend the drug and polymer. In some preferred examples, the solvent or solvent combination completely dissolves the drug and polymer.

In some preferred embodiments, the solvent includes a mixture of methylene chloride and acetone.

In some embodiments, the glacial acetic acid is present as a component in a solvent from about 0.1% to about 20% by wt (e.g., from about 3% to about 15%, from about 4% to about 12%, or from about 5% to about 10%).

In some embodiments, the solvent comprises a mixture of methylene chloride, acetone, and glacial acetic acid.

In some embodiments, the solvent system comprises from about 40% to about 80% methylene chloride, from about 20% to about 35% acetone, and from about 0.1% to about 15% glacial acetic acid (e.g., from about 50% to about 70% methylene chloride, from about 25% to about 30% acetone, and from about 3% to about 12% glacial acetic acid).

In some embodiments, the mixture also includes a surfactant, for example, sodium lauryl sulfate (SLS) or Vitamin E or a derivative thereof (e.g., Vitamin E TPGS).

In some preferred embodiments, the solvent includes a mixture of methylene chloride and acetone. In some embodiments, the water is present as a component in a solvent from about 0.1% to about 20% by wt (e.g., from about 3% to about 15%, from about 4% to about 12%, or from about 1% to about 10%).

In some embodiments, the solvent comprises a mixture of methylene chloride, acetone, and water.

In some embodiments, the solvent system comprises from about 40% to about 80% methylene chloride, from about 20% to about 35% acetone, and from about 0.1% to about 15% water (e.g., from about 50% to about 70% methylene chloride, from about 25% to about 30% acetone, and from about 1% to about 5% water).

In some embodiments, the mixture also includes a surfactant, for example, sodium lauryl sulfate (SLS) or Vitamin E or a derivative thereof (e.g., Vitamin E TPGS).

In one aspect, the disclosure provides product made by a process described herein. For example a solid dispersion of a drug (e.g., VX-950), such as an amorphous solid dispersion of a drug (e.g., VX-590). For example an amorphous solid dispersion including a drug (e.g., VX-950), at least one polymer, and optionally one or more solubility enhancing surfactant (e.g., SLS or Vitamin E TPGS) is provided. The dispersion can enhance the aqueous solubility and bioavailability of the drug (e.g., VX-950) upon oral dosing of the solid dispersion to a mammal (e.g., a rat, dog or human). In certain aspects, at least a portion of the drug (e.g., VX-950) in the solid dispersion is in the amorphous state (e.g., at least about 50%, at least about 55%, at least about 60%, at least about 65%, at least about 70%, at least about 75%, at least about 80%, at least about 85%, at least about 90%, at least about 95%, at least about 98%, or at least about 99%). In preferred embodiments, the solid dispersion is essentially or substantially free of crystalline drug (e.g., VX-950).

In a preferred embodiment, the solid dispersion made by a process described herein includes about 45% to about 85% VX-950, about 5% to about 25% of an HPMC polymer, such as HPMC60SH50, about 5% to about 30% of an HPMCAS polymer, such as HPMCAS-HG, and about 0.1% to about 10% of a surfactant, such as SLS or vitamin E or a derivative thereof (e.g., vitamin E TPGS), wherein the HPMC and HPMCAS together account for about 90%, about 95%, about 98%, about 99%, or about 100% of the total polymer present.

In a preferred embodiment, the solid dispersion made by a process described herein exhibits a predetermined level of physical and/or chemical stability. E.g., the solid dispersion retains about 50%, about 60%, about 70%, about 80%, about 90%, about 95%, about 98%, or about 99%, of amorphous VX-950 when stored at 25° C. in a closed water tight container, e.g., an amber glass vial or high density polyethylene (HDPE) container.

As would be appreciated, spray drying may be done in the presence of an inert gas. In certain embodiments, processes that involve spray drying may be done in the presence of a supercritical fluid involving carbon dioxide or a mixture of carbon dioxide.

A "poorly soluble drug" as used herein means drugs that are essentially totally water-insoluble or sparingly water-soluble. The term applies to any beneficial therapeutic agent having a dose (mg) to aqueous solubility (mg/ml) ratio greater than 100 ml, where the drug solubility is that of the neutral (e.g., free base or free acid) form in unbuffered water. This definition includes but is not limited to drugs that have essentially no aqueous solubility (less than 1.0 μg/ml).

The details of one or more embodiments of the invention are set forth in the description below. Other features, objects, and advantages of the invention will be apparent from the description and from the claims.

BRIEF DESCRIPTION OF THE DRAWINGS

FIG. 3 is a table providing the properties of VX-950 solid dispersions that were spray dried in a solvent system that contained water.

DETAILED DESCRIPTION

Methods of Spray Drying

Figure 1:
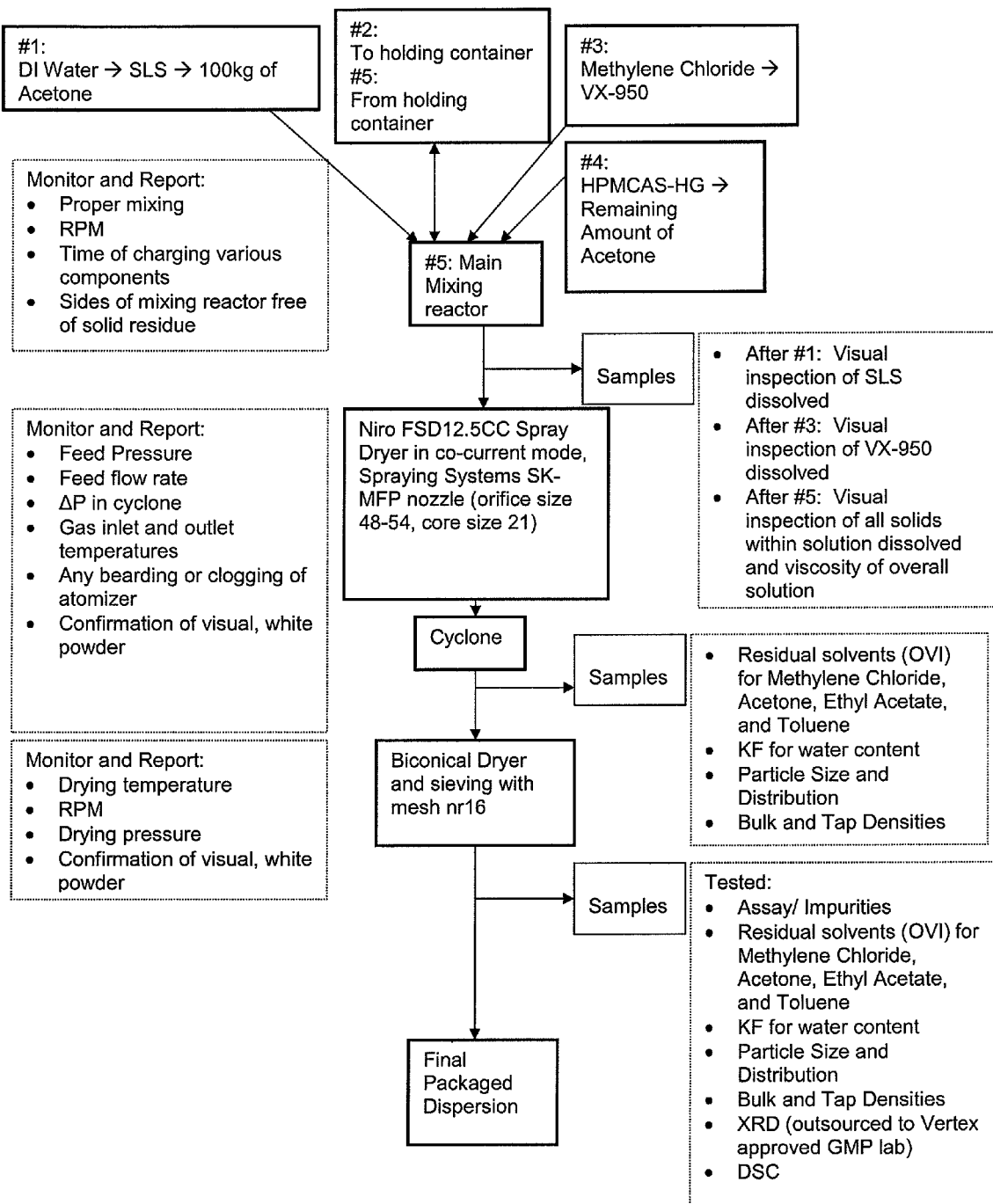
FIG. 1 is a flowchart schematic of a spray drying manufacturing process, control, sampling, and testing.

Spray Drying.

A preferred embodiment of this invention involves an amorphous solid dispersion obtained by spray-drying where the solvent mixture of the starting material includes at least one non-volatile solvent (e.g., glacial acetic acid or water). Accordingly, in another embodiment, this invention provides drying the product obtained by spray drying to remove the solvent.

A pharmaceutical composition, can be obtained by spray-drying a mixture comprising a drug (e.g., VX-950), a suitable polymer(s), and an appropriate solvent system. Spray drying is a method that involves atomization of a liquid mixture containing, e.g., a solid and a solvent, and removal of the solvent. Atomization may be done, for example, through a nozzle or on a rotating disk.

Spray drying is a process that converts a liquid feed to a dried particulate form. Optionally, a secondary drying process such as fluidized bed drying or vacuum drying, may be used to reduce residual solvents to pharmaceutically acceptable levels. Typically, spray-drying involves contacting a highly dispersed liquid suspension or solution, and a sufficient volume of hot air or gas to produce evaporation and drying of the liquid droplets. The preparation to be spray dried can be any solution, suspension, coarse suspension, slurry, colloidal dispersion, or paste that may be atomized using the selected spray-drying apparatus. In a standard procedure, the preparation is sprayed into a current of warm filtered air or gas that evaporates the solvent and conveys the dried product to a collector (e.g., a cyclone or directly to a membrane filter bag). The spent air is then exhausted with the solvent, or alternatively the spent air is sent to a condenser to capture and potentially recycle the solvent. Commercially available types of apparatus may be used to conduct the spray-drying. For example, commercial spray dryers are manufactured by Buchi Ltd. and Niro (e.g., the PSD line of spray driers manufactured by Niro) (see, US 2004/0105820; US 2003/0144257). For example, a pressure nozzle, a two-fluid electrosonic nozzle, a two-fluid nozzle, or a rotary atomizer can be used.

Spray-drying typically employs solids loads of material from about 0.5% to about 30%, (i.e., drug plus and excipients) preferably at least about 10%. In some embodiments, loads of less than 10% may result in light or porous dispersion or low bulk densities or unacceptably long run-times. In general, the upper limit of solids loads is governed by the viscosity of (e.g., the ability to pump) the resulting solution and the solubility of the components in the solution. Generally, the viscosity of the solution can determine the size of the particle in the resulting powder product.

Techniques and methods for spray-drying may be found in Perry's Chemical Engineering Handbook, 6th Ed., R. H. Perry, D. W. Green & J. O. Maloney, eds.), McGraw-Hill book co. (1984); and Marshall "Atomization and Spray-Drying" 50, Chem. Eng. Prog. Monogr. Series 2 (1954). In general, the spray-drying is conducted with an inlet temperature of from about 40° C. to about 200° C., for example, from about 45° C. to about 150° C., preferably from about 50° C. to about 100° C., e.g., about 50° C. The spray-drying is generally conducted with an outlet temperature of from about 15° C. to about 100° C., for example from about 20° C. to about 75° C., e.g., about 27° C.

Removal of the solvent may require a subsequent drying step, such as tray drying, fluid bed drying (e.g., from about room temperature to about 100° C., e.g., about 60° C.), vacuum drying, microwave drying, rotary drum drying or biconical vacuum drying (e.g., from about room temperature to about 100° C., e.g., about 60° C. or lower).

Fluidized Spray Drying.

Another preferred embodiment of this invention involves an amorphous solid dispersion obtained by fluidized spray drying where the solvent mixture of the starting material includes at least one non-volatile solvent (e.g., glacial acetic acid or water). Accordingly, in another embodiment, this invention provides drying the product obtained by fluidized spray drying to remove the solvent.

The process of fluidized spray drying combines spray drying and fluid bed drying technologies. Agglomerated powders are obtained based on the integrated fluid bed or belt and a multi-stage process where moist powder, produced during the first drying stage, forms agglomerates, which are post-dried and cooled in the following stages. Briefly, a pressure nozzle, a two-fluid electrosonic nozzle, a two-fluid nozzle, or a rotary atomizer sprays the feed down into the spray dryer towards the fluid bed. Agglomeration incorporating finer, recycled material takes place in the spray dryer, and agglomerated particles fall to the bed. Exhaust air outlet is through the roof causing further agglomeration in the zone of spraying. Sticky products can be dried successfully, and the process is ideal for drying heat sensitive products, and improved aroma retention is accomplished. The process yields agglomerated, free-flowing powders with minimal fines.

As an example, in the spray dryer, feed is sprayed from the atomization nozzle mounted on top of the drying chamber into the drying air and down the spray chamber. The vigorous fluidization of moist powder in the fluid bed located at the chamber base, plus recycle of fines from the cyclone attachment, result in spray drying taking place in a powder-laden atmosphere. Particles of higher moisture content can be handled in the drying chamber due to the resulting powdering effect overcoming the problems of powder stickiness. Drying can be completed at lower powder and exhaust air temperatures, thus improving product quality while gaining from a higher thermal efficiency. The degree of agglomeration and thus the particle size distribution can be influenced by changing the operation conditions and the location where fines are re-introduced into the drying chamber. By optimizing the operation conditions, a dispersion with properties favorable for downstream processing (e.g., direct compression), can be obtained.

As with conventional spray drying, a non-volatile solvent (e.g., glacial acetic acid, DMSO, DMF, or water) can be used in the FSD process.

Although embodiments of the present disclosure refer to the use of non-volatile solvents with spray drying, it is to be understood that the process of fluidized spray drying is also applicable and can be used in the embodiments described herein.

A detailed description of fluidized spray drying of VX-950 is provided in the provisional application filed on Dec. 22, 2006, entitled Fluidized Spray Drying, U.S. Provisional Application No. 60/871,695.

Solvents

In general, there is a direct relationship between bulk density/flow and residual solvent; the higher the bulk density/better flow, the higher the residual solvent. In some instances, the particle size and density can be manipulated by varying the amount of time taken for the particle to solidify and/or dry. Accordingly, inclusion of a non-volatile (or high boiling) solvent into the mixture can provide for a particle product having improved properties. For example, the addition of glacial acetic acid or water into a solvent system comprising volatile organic solvents can provide larger and/or more dense particles than the particles produces without the glacial acetic acid or water. The larger and/or more dense particles can have improved flow properties, which is desirable for downstream formulation of the particles, for example into an oral dosage form such as a tablet or capsule. In some embodiments, the solvent system provides particles that solidify after at least about 5 seconds, at least about 7 seconds, at least about 10 seconds, at least about 12 seconds, at least about 15 seconds, at least about 20 seconds, or more.

Additionally, it may be advantageous to optimize the powder flow and bulk density and/or use secondary drying to remove the residual solvent. In one embodiment of this invention, the solid dispersion is fluid-bed dried. Fluid-bed drying at about 40° C. to about 80° C., e.g., about 40° C. to about 60° C., e.g., about 45° C. for about 8 hours has been found effective in certain embodiments to provide optimal effects in certain solid dispersion of VX-950. In other embodiments, e.g., using HPMCAS as the polymer in the solid dispersion, fluid-bed drying at 45° C. for about 4 hours has been effective to provide acceptable levels of residual solvent in the final product.

In preferred processes, the solvent includes a volatile solvent and a non-volatile solvent. In some embodiments, the solvent includes a mixture of volatile solvents. Preferable solvents include those that can dissolve both VX-950 and the polymer (when present) and/or a surfactant (when present). Suitable solvents include those described above, for example, methylene chloride, acetone, etc.

In embodiments where VX-950 is being spray dried or undergoes fluidized spray drying, preferred solvents include a mixture of methylene chloride, acetone, and glacial acetic acid.

In other embodiments where VX-950 is being spray dried or undergoes fluidized spray drying, preferred solvents include a mixture of methylene chloride, acetone, and water.

In some cases, a solvent may react with a material (e.g., compound of interest, e.g., drug or therapeutic agent) being spray dried. Therefore, in some embodiments, a solvent that does not react with the compound of interest is preferred when preparing a feed solution containing that compound. For example, alcohols may react with the compound of interest (e.g., a drug, e.g., a poorly soluble drug, e.g., VX-950) to form ketals. Accordingly, a solvent that does not react with the compound of interest (e.g., a drug, e.g., a poorly soluble drug, e.g., VX-950) (particularly to form ketals) is preferred when preparing a feed solution containing that compound. Such a solvent should not contain an OH group or a similarly reactive moiety. Because of the reactivity of certain compounds (e.g., VX-950), a preferred solvent for use in the solvent system in connection with this disclosure for the preparation of a feed solution containing such a compound is other than a polyethylene glycol (e.g., PEG 8000) (i.e., other than a polymer having free hydroxyl moieties).

In another preferred embodiment, the non-volatile solvent is water. An exemplary percent weight ratio of methylene chloride to acetone to water is 75:24:1.

In some instances, the non-volatile solvent (e.g., water) can contribute to solubilizing a component, e.g., a surfactant (e.g., SLS), that is present in the mixture undergoing spray drying.

In another preferred embodiment, the non-volatile solvent (e.g., water) has a higher bulk density.

In some embodiments, the non-volatile solvent is a component in a solvent mixture. For example, the non-volatile solvent is present as a component in a solvent from about 1% to about 20% by weight (e.g., from about 1% to about 5%, from about 3% to about 15%, from about 4% to about 12%, or from about 5% to about 10%). In other embodiment, the non-volatile solvent (e.g., water) is present in an amount of between about 0% and about 5%, e.g., about 1%.

In some preferred embodiments, the solvent mixture is a combination of a volatile solvent or combination of solvents such as methylene chloride and acetone with a non-volatile solvent such as water or glacial acetic acid. For example, the solvent mixture comprises from about 40% to about 80% methylene chloride, from about 20% to about 35% acetone, and from about 1% to about 15% glacial acetic acid (e.g., from about 50% to about 70% methylene chloride, from about 25% to about 30% acetone, and from about 3% to about 12% glacial acetic acid). As another example, the solvent mixture comprises from about 40% to about 80% methylene chloride, from about 20% to about 35% acetone, and from about 1% to about 15% water (e.g., from about 50% to about 70% methylene chloride, from about 25% to about 30% acetone, and from about 1% to about 5% water). An exemplary percent weight ratio of methylene chloride to acetone to non-volatile solvent (e.g., water) is 75:24:1.

Because of the reactivity of VX-950, a preferred polymer in embodiments including VX-950 is other than a polyethylene glycol (e.g., PEG 8000) (i.e., other than a polymer having free hydroxyl moieties).

The solvent, particle size and the temperature drying range may be modified to prepare an optimal solid dispersion. As would be appreciated by skilled practitioners, a small particle size would lead to faster solvent removal. Applicants have found however that smaller particles can lead to fluffy particles that do not provide optimal solid dispersions for downstream processing such as tableting. At higher temperatures, crystallization or chemical degradation of VX-950 may occur. At lower temperatures, a sufficient amount of the solvent may not be removed.

Particle size distribution and densities (e.g., bulk and/or tap densities) can be optimized, e.g., by varying one or more of the following parameters: outlet temperature, and feed pressure. The suitability of a parameter variation can be evaluated. For example, to evaluate the suitability of the outlet temperature, the temperature can be increased (e.g., to 30° C.) while keeping all other process parameters unchanged. The properties (e.g., densities) of the dispersion obtained from spray drying using this increased temperature are compared to the properties of a dispersion made according to this disclosure (e.g., outlet temperature of 25° C.), and an evaluation can be made as to whether the temperature change was advantageous (e.g., if the change led to an increase in a desired property (e.g., increased bulk density), then the change may be advantageous).

Other parameters that can be varied and optimized (e.g., in an analogous manner) for the spray drying process include: choice of non-volatile solvent, percentage of non-volatile solvent used, choice of volatile solvent(s), percentage of volatile solvent(s) used (e.g., total percentage and/or ratio of each volatile solvent to the other if more than one volatile solvent is used), choice of surfactant, percentage of surfactant used, choice of polymer, percentage of polymer used, choice of atomizer, solution feedrate, cyclone pressure differential, order of solids addition, percentage of solids loading, and/or inlet temperature. If post-spray drying is performed, the following can be optimized: choice of drying process, duration of drying process, dryer rotation speed, drying temperature, drying pressure, and/or drying time.

The nature of the solvent can be modified to optimize particle size and density. For example, increasing the amount of a high boiling (or non volatile) solvent component in the solvent can increase the length of time required for solidification and/or drying of the resulting spray dried particles. Therefore, in instances where it is desirable to have larger and/or more dense particles, an increased amount of high boiling (or non-volatile) solvent is desirable. The nature of the high boiling or non-volatile solvent can also be varied depending on the desired properties of the dispersed particle and/or the properties of the drug. For example, desirable high boiling or non-volatile solvents improve the solubility of the drug or other component (e.g., surfactant, e.g., SLS; or polymer) in the solution and do not chemically react with or contribute to the chemical degradation of the drug (or surfactant or polymer, if present). For example, organic acid solvent would not be appropriate for a drug that is acid sensitive or which has an acid labile moiety. The methods herein provide a optimal particle size and an optimal drying temperature.

Examples of volatile solvents include ketones, alcohols, acetonitrile, methylene chloride, acetone, chloroform, and THF. As will be appreciated by the skilled artisan, the selection of solvents depends, at least in part, on the solubility of the composition (e.g., drug or other therapeutic agent) in a solvent and/or the reactivity of the composition (e.g., functional group) with a particular solvent.

Examples of non-volatile solvents include organic acids such as toluene, glacial acetic acid, DMSO, DMF, and water. The selection of solvents can depend, at least in part, on the solubility of the composition (e.g., drug or other therapeutic agent) in a solvent and/or the reactivity of the composition (e.g., functional group) with a particular solvent. As used herein, the term "non-volatile solvent" refers to a liquid that has a boiling point greater than 80° C. at 1 atm.

To evaluate the suitability of a solvent, the choice of solvent can be changed while keeping all other process parameters unchanged. The properties (e.g., densities) of the dispersion obtained from spray drying using this changed solvent are compared to the properties of a dispersion made according to this disclosure using a solvent described herein (e.g., water as a non-volatile solvent), and an evaluation can be made as to whether the solvent change was advantageous (e.g., if the change led to an increase in a desired property (e.g., increased bulk density), then the change may be advantageous). In like manner, the amount used of a given solvent (e.g., water as a non-volatile solvent) can also be evaluated, e.g., by comparing the resulting product to a product produced using a solvent described herein in an amount described herein, e.g., 1% water as a non-volatile solvent.

Polymers

Products (e.g., agglomerated products such as powders or granules) being spray dried or undergoing fluidized spray drying, such as solid dispersions (e.g., amorphous solid dispersions) including a compound of interest (e.g., a drug, e.g., a poorly soluble drug, e.g., VX-950) may include a polymer or plurality of polymers (or solid state carrier(s)).

Methods of spray drying and FSD utilizing a non-volatile solvent described herein may be used to prepare a solid dispersion (e.g., amorphous solid dispersion) that contains a compound of interest (e.g., a drug, e.g., a poorly soluble drug, e.g., VX-950). In addition, the mixture that contains the solvents (e.g., volatile and non-volatile solvents) and compound of interest (e.g., drug) that will be dried may also contain a polymer or plurality of polymers (or solid state carrier(s)).

A polymer or plurality of polymers can be used as part of an amorphous solid dispersion system together with compound of interest. For example, a polymer(s) can be present in a feed solution (e.g., that will be dried by FSD) with a compound of interest (e.g., drug). Without being bound by theory, the presence of a polymer can help prevent, decrease, or slow the amount or rate of crystallization of the compound of interest (e.g., drug) as compared to the amount or rate of crystallization that occurs in the absence of a polymer. For example, when a polymer is used, the amount of crystallization can be decreased by at least about 10%, by at least about 20%, by at least about 30%, by at least about 40%, by at least about 50%, by at least about 60%, by at least about 70%, by at least about 80%, by at least about 90%, by at least about 95%, or by at least about 99% compared to the amount of crystallization in the absence of a polymer. For example, a polymer or plurality of polymers can protect a drug against crystallization in an aqueous medium, such as gastric fluids and/or in intestinal fluids. For example, HPMC can help decrease the amount of crystallization (e.g., of a compound of interest (e.g., a drug, e.g., a poorly soluble drug, e.g., VX-950)) in low pH, such as in gastric fluids. HPMC can provide protection in gastric fluids (e.g., fasted or fed gastric fluids), and simulated gastric fluids ("SGF") (e.g., fasted or fed SGF). As another example, HPMCAS can provide increased physical stability and decrease the amount of crystallization (e.g., a compound of interest (e.g., a drug, e.g., a poorly soluble drug, e.g., VX-950)) in intestinal fluids (e.g., fasted or fed intestinal fluids) and simulated intestinal fluids ("SIF") (e.g., fasted or fed SIF). As a result, one or more of bioavailability, solubility and absorption of the compound of interest (e.g., a drug, e.g., a poorly soluble drug, e.g., VX-950) can be enhanced.

In addition, by decreasing the rate of crystallization, a polymer can increase the shelf stability of a composition, e.g., a dispersion obtained by spray drying or FSD or a solid form (e.g., a directly compressed form, e.g., a tablet), containing a compound of interest (e.g., a drug, e.g., a poorly soluble drug, e.g., VX-950) relative to the stability of the composition when no polymer is used by at least about 10% (e.g., by at least about 20%, by at least about 30%, by at least about 40%, by at least about 50%, by at least about 60%, by at least about 70%, by at least about 80%, or by at least about 90%). The polymer can increase the stability of the solid dispersion (e.g., when stored at 4° C. or at room temperature) by at least about 10% (e.g., by at least about 20%, by at least about 30%, by at least about 40%, by at least about 50%, by at least about 60%, by at least about 70%, by at least about 80%, or by at least about 90%) as compared to a solid dispersion stored under identical conditions and in the absence of a polymer.

Further, without being bound by theory, the presence of a plurality of polymers can help prevent, decrease, or slow the amount or rate of crystallization of the compound of interest (e.g., a drug, e.g., a poorly soluble drug, e.g., VX-950) as compared to the amount or rate of crystallization that occurs in the presence of one polymer. For example, when a plurality of polymers is used, the amount of crystallization can be decreased by at least about 10%, by at least about 20%, by at least about 30%, by at least about 40%, by at least about 50%, by at least about 60%, by at least about 70%, by at least about 80%, by at least about 90%, by at least about 95%, or by at least about 99% compared to the amount of crystallization in the presence of one polymer. For example, a plurality of polymers can protect a drug against crystallization in an aqueous medium, such as gastric fluids or in intestinal fluids. For example, a polymer, e.g., HMPC or HPMCAS, or plurality of polymers, e.g., a mixture comprising HPMC and HPMCAS, can offer increased protection to a given dispersion of VX-950: for example, the HMPC can protect the VX-950 from crystallization in gastric fluids or SGF while the HPMCAS can protect the VX-950 from crystallization in intestinal fluids or in SIF. As a result, use of a mixture can offer improved bioavailability, solubility, and/or absorption of a compound of interest (e.g., a drug, e.g., a poorly soluble drug, e.g., VX-950). In addition, a plurality of polymers can increase the shelf stability of a composition, e.g., a solid form (e.g., a spray dried dispersion, a directly compressed dosage form, e.g., a tablet), containing a compound of interest (e.g., a drug, e.g., a poorly soluble drug, e.g., VX-950) relative to the stability of the composition when no polymer is used by at least about 10% (e.g., by at least about 20%, by at least about 30%, by at least about 40%, by at least about 50%, by at least about 60%, by at least about 70%, by at least about 80%, or by at least about 90%). The plurality of polymers can increase the stability of the solid dispersion (e.g., when stored at 4° C. or at room temperature) by at least about 10% (e.g., by at least about 20%, by at least about 30%, by at least about 40%, by at least about 50%, by at least about 60%, by at least about 70%, by at least about 80%, or by at least about 90%) as compared to a solid dispersion stored under identical conditions and containing no polymer.

The polymer or plurality of polymers (e.g., containing one or more cellulosic polymers) can be used to provide a form of a compound of interest (e.g., a drug, e.g., a poorly soluble drug, e.g., VX-950) such that, when administered, the area under curve (AUC) of the compound of interest (e.g., a drug, e.g., a poorly soluble drug, e.g., VX-950) would be substantially the same in fasted and fed subjects, e.g., reducing or substantially eliminating the food effect in the subject.

In one embodiment, a polymer or plurality of polymers, or one or more of the polymers in a plurality of polymers of the present disclosure are able to dissolve in aqueous media. The solubility of the polymer(s) may be pH-independent or pH-dependent. The latter include one or more enteric polymers. The term "enteric polymer" refers to a polymer that is preferentially soluble in the less acidic environment of the intestine relative to the more acid environment of the stomach, for example, a polymer that is insoluble in acidic aqueous media but soluble when the pH is above 5-6. An appropriate polymer should be chemically and biologically inert. In order to improve the physical stability of the solid dispersions, the glass transition temperature ($T_g$) of the polymer or polymers (e.g., of a plurality of polymers, or one or more of the polymers in a plurality of polymers) should be as high as possible. For example, preferred polymers have a glass transition temperature at least equal to or greater than the glass transition temperature of the compound of interest (e.g., a drug, e.g., a poorly soluble drug, e.g., VX-950). Other preferred polymers have a glass transition temperature that is within about 10 to about 15° C. of the compound of interest (e.g., a drug, e.g., a poorly soluble drug, e.g., VX-950). Examples of suitable glass transition temperatures of the polymers include at least about 55° C., at least about 60° C., at least about 65° C., at least about 70° C., at least about 75° C., at least about 80° C., at least about 85° C., at least about 90° C., at least about 95° C., at least about 100° C., at least about 105° C., at least about 110° C., at least about 115° C., at least about 120° C., at least about 125° C., at least about 130° C., at least about 135° C., at least about 140° C., at least about 145° C., at least about 150° C., at least about 155° C., at least about 160° C., at least about 165° C., at least about 170° C., or at least about 175° C. (as measured under dry conditions). Without wishing to be bound by theory, it is believed that the underlying mechanism is that a polymer with a higher $T_g$ generally has lower molecular mobility at room temperature, which can be a crucial factor in stabilizing the physical stability of the amorphous solid dispersion.

Additionally, the hygroscopicity of the polymer (or of a plurality of polymers, or one or more of the polymers in a plurality of polymers) should be as low as possible. For the purpose of comparison in this application, the hygroscopicity of a polymer, combination of polymers, or composition is characterized at about 60% relative humidity. In some preferred embodiments, the polymer(s) has less than about 10% water absorption, for example less than about 9%, less than about 8%, less than about 7%, less than about 6%, less than about 5%, less than about 4%, less than about 3%, or less than about 2% water absorption. Cellulosic polymers generally have about 3% water absorption whereas PVP generally has about 9% water absorption. The hygroscopicity can also affect the physical stability of the solid dispersions. Generally, moisture adsorbed in the polymers can greatly reduce the $T_g$ of the polymers as well as the resulting solid dispersions, which will further reduce the physical stability of the solid dispersions as described above.

In one embodiment, a polymer or plurality of polymers, or one or more of the polymers in a plurality of polymers is one or more water-soluble polymer(s) or partially water-soluble polymer(s). Water-soluble or partially water-soluble polymers include but are not limited to, cellulose derivatives (e.g., hydroxypropylmethylcellulose (HPMC; also known as hypromellose), hydroxypropylcellulose (HPC)) or ethylcellulose; polyvinylpyrrolidones (PVP); polyethylene glycols (PEG); polyvinyl alcohols (PVA); acrylates, such as polymethacrylate (e.g., EUDRAGIT® E); cyclodextrins (e.g., β-cyclodextin) and copolymers and derivatives thereof, including for example PVP-VA (polyvinylpyrrolidone-vinyl acetate). In some preferred embodiments, the polymer or one of the plurality of polymers is hydroxypropylmethylcellulose (HPMC), such as HPMC E50 (e.g., from Dow), HPMCE15, or HPMC 60SH 50cP (e.g., Shin-Etsu Metolose, HPMC60SH50). HPMC is available in a variety of types from Shin-Etsu, including SM, 60SH, 65SH, 90SH. Each of these types vary by viscosity grade and methoxyl and hydroxypropoxyl content. A most preferred type for use in the spray dispersion is HPMC 60SH.

In some embodiments, the polymer or plurality of polymers, or one or more of the polymers in a plurality of polymers are a pH-dependent enteric polymer. Such pH-dependent enteric polymers include, but are not limited to, cellulose derivatives (e.g., cellulose acetate phthalate (CAP)), hydroxypropyl methyl cellulose phthalates (HPMCP), hydroxypropyl methyl cellulose acetate succinate (HPMCAS), hydroxypropyl methyl cellulose acetate (HPMCA), carboxymethylcellulose (CMC) or a salt thereof (e.g., a sodium salt such as (CMC-Na)); cellulose acetate trimellitate (CAT), hydroxypropylcellulose acetate phthalate (HPCAP), hydroxypropylmethyl-cellulose acetate phthalate (HPMCAP), and methylcellulose acetate phthalate (MCAP), or polymethacrylates (e.g., EUDRAGIT® S). In some preferred embodiments, the polymer or one of the plurality of polymers is hydroxypropyl methyl cellulose acetate succinate (HPMCAS). HPMCAS is available in a variety of grades from Shin-Etsu, including AS-LF, AS-MF, AS-HF, AS-LG, AS-MG, AS-HG. Each of these grades vary with the percent substitution of acetate and succinate. A most preferred grade for use in the spray dispersion is AS-HG from Shin-Etsu.

Other polymers of HPMCAS and HPMCA with varying degrees and combinations of substitution of hydroxypropoxy, methoxy, acetyl, and succinoyl groups are also known in the art (see e.g., WO 2005/115330), and can be used with the inventions described herein. For example, HPMCAS polymers where the degree of substitution of succinoyl groups ($DOS_S$) and the degree of substitution of acetyl groups ($DOS_{Ac}$) on the HPMCAS are $DOS_S \geq$ about 0.02, $DOS_{Ac} \geq$ about 0.65, and $DOS_{Ac} + DOS_S \geq$ about 0.85 can be used. As other examples, HPMCA polymers where the degree of substitution of acetyl groups ($DOS_{Ac}$) on the polymer is about 0.6 or less, or the degree of substitution of acetyl groups ($DOS_{Ac}$) on the polymer is at least about 0.15, can be used. In other embodiments, HPMCA polymers having a solubility parameter of about 24.0 (J/cm) or less can be used.

In yet another embodiment, the polymer or one or more of the polymers in a plurality of polymers is an insoluble cross-linked polymer, for example a polyvinylpyrrolidone (e.g., Crospovidone).

In some cases, a polymer may react with a compound of interest. Therefore, in some embodiments, a polymer that does not react with the compound of interest is preferred when preparing a feed solution containing that compound. For example, alcohols may react with the compound of interest (e.g., a drug, e.g., a poorly soluble drug, e.g., VX-950) to form ketals. Accordingly, a polymer that does not react with the compound of interest (e.g., a drug, e.g., a poorly soluble drug, e.g., VX-950) (particularly to form ketals) is preferred when preparing a feed solution containing that compound. Such a polymer should not contain an OH group or a similarly reactive moiety. Because of the reactivity of certain compounds (e.g., VX-950), a preferred polymer for use in a plurality of polymers or as the polymer in connection with this disclosure for the preparation of a feed solution containing such a compound is other than a polyethylene glycol (e.g., PEG 8000) (i.e., other than a polymer having free hydroxyl moieties).

In embodiments where the compound of interest (e.g., a drug, e.g., a poorly soluble drug, e.g., VX-950) forms a solid dispersion (e.g., agglomerated product) with a polymer or plurality of polymers, for example VX-950 with an HPMC and/or an HPMCAS polymer, the total amount of polymer(s) relative to the total weight of the solid dispersion is typically at least about 5% (e.g., about 4% or 6%), at least about 10% (e.g., 9% or 11%), at least about 15% (e.g., 14% or 16%), at least about 20% (e.g., 19% or 21%), and preferably at least about 30% (e.g., about 29% or 31%), for example, at least about 35% (e.g., about 34% or 36%), at least about 40% (e.g., about 39% or 41%), at least about 45% (e.g., about 44% or 46%), or at least about 50% (e.g., about 49% or 51%). The amount is typically about 99% or less, and preferably about 80% or less, for example about 75% or less, about 70% or less, about 65% or less, about 60% or less, or about 55% or less. In one embodiment, the polymer(s) is in an amount of up to about 30% of the total weight of the dispersion (and even more specifically, between about 28% and 32%, such as about 29%). In one embodiment, the polymer(s) is in an amount of up to about 35% of the total weight of the dispersion (and even more specifically, between about 33% and 37%, such as about 34%). In one embodiment, the polymer(s) is in an amount of up to about 40% of the total weight of the dispersion (and even more specifically, between about 38% and 42%, such as about 39%). In one embodiment, the polymer(s) is in an amount of up to about 45% of the total weight of the dispersion (and even more specifically, between about 43% and 47%, such as about 44%).

The solid dispersions (e.g., agglomerated products) containing a compound of interest (e.g., a drug, e.g., a poorly soluble drug, e.g., VX-950) can contain a plurality of polymers. For example, two polymers can be used in the dispersion. In some embodiments, the plurality of polymers can include one or more than one cellulosic polymer. For example, a spray dried dispersion can include two cellulosic polymers, e.g., HPMC and HPMCAS. In some embodiments, the solid dispersion includes a mixture of HPMC and HPMCAS. The amount of each polymer used in the dispersion can vary, and the ratio of the polymers to each other can also vary. For example, the dispersion can include from about 0% to about 100% by weight of a first polymer (e.g., HPMC) and from about 0% to about 100% by weight of a second polymer (e.g., HPMCAS) (wherein the percentages by weight of the two polymers add up to 100% of total polymer present in a dispersion). For example, in a solid dispersion of VX-950 containing polymers, the first polymer is present in an amount of about 33% and the second polymer is present in an amount of about 67% of the total amount of polymer added. In another example, the first polymer is present in an amount of about 55.5% and the second polymer is present in an amount of about 44.5% of the total amount of polymer added. In another example, the first polymer is present in an amount of about 63% and the second polymer is present in an amount of about 37% of the total amount of polymer added. In another example, the first polymer is present in an amount of about 50% and the second polymer is present in an amount of about 50% of the total amount of polymer added. In another example, the first polymer is present in an amount of about 100% and the second polymer is present in an amount of about 0% of the total amount of polymer added.

In one of the more specific embodiments of this disclosure, one of the polymers is polyvinylpyrrolidone (PVP) (e.g., PVP29/32). The PVP can be present in an amount of up to about 35%, up to about 40%, up to about 45%, or up to about 50%. A dispersion comprising about 50% (e.g., about 49.5%) PVP K29/32 is included within this disclosure.

In another embodiment, the disclosure includes a solid dispersion (e.g., agglomerated product) of a compound of interest (e.g., a drug, e.g., a poorly soluble drug, e.g., VX-950) and a cellulosic polymer, for example an HPMC or an HPMCAS polymer. In some preferred embodiments, the compound (i.e., VX-950) is present in an amount of at least about 50% of the dispersion, for example at least about 55%, at least about 60%, at least about 65%, at least about 70%, at least about 75%, at least about 80%, at least about 85%, at least about 90%, or even greater. In some preferred embodiments, the drug is present in an amount between about 55% and about 90%, such as about 55%, about 60%, about 65%, about 70%, about 75%, about 80%, or about 85%. The amount of polymers is present in an amount of at least about 5%, at least about 10%, at least about 15%, and preferably at least about 20%, for example, at least about 25%, at least about 30%, at least about 35%, at least about 40%, or at least about 45%. In some embodiments, the amount is typically about 55% or less, and preferably about 50% or less, for example about 45% or less, about 40% or less, about 35% or less, about 30% or less, about 25% or less, about 20% or less, about 15% or less, or about 10% or less.

In another embodiment, the disclosure includes a solid dispersion (e.g., agglomerated product) of a compound of interest (e.g., a drug, e.g., a poorly soluble drug, e.g., VX-950) and at least two cellulosic polymers, for example an HPMC and/or an HPMCAS polymer. In some preferred embodiments, the compound (i.e., VX-950) is present in an amount of at least about 50% of the dispersion, for example at least about 55%, at least about 60%, at least about 65%, at least about 70%, at least about 75%, at least about 80%, at least about 85%, at least about 90%, or even greater. In some preferred embodiments, the drug is present in an amount between about 55% and about 70%, such as about 55%, about 60%, about 65%, or about 70%. As described above, the total amount of polymers is present in an amount of at least about 15%, and preferably at least about 20%, for example, at least about 25%, at least about 30%, at least about 35%, at least about 40%, or at least about 45%. In some embodiments, the amount is typically about 55% or less, and preferably about 50% or less, for example about 45% or less, about 40% or less, about 35% or less, about 30% or less, about 25% or less, about 20% or less, about 15% or less, or about 10% or less.

In some preferred embodiments, the dispersion further includes other minor ingredients, such as a surfactant (e.g., SLS or Vitamin E TPGS). In some preferred embodiments, the surfactant is present in less than about 10% by weight of the dispersion, for example less than about 9% by weight, less than about 8% by weight, less than about 7% by weight, less than about 6% by weight, less than about 5% by weight, less than about 4% by weight, less than about 3% by weight, less than about 2% by weight, or about 1% by weight.

In a most preferred embodiment, the dispersion includes about 49.5% VX-950, about 49.5% HPMCAS, and about 1% SLS.

The polymer or plurality of polymers should be present in an amount effective for stabilizing the solid dispersion. Stabilizing includes inhibiting or decreasing the crystallization of a compound of interest (e.g., a drug, e.g., a poorly soluble drug, e.g., VX-950). Such stabilizing would inhibit the conversion of the compound from amorphous to crystalline form. For example, the polymer(s) would prevent at least a portion (e.g., about 5%, about 10%, about 15%, about 20%, about 25%, about 30%, about 35%, about 40%, about 45%, about 50%, about 55%, about 60%, about 65%, about 70%, about 75%, or greater) of the compound from going from an amorphous to a crystalline form.

For example, at low pH (e.g., in gastric fluid (e.g., fasted gastric fluid) or SGF (e.g., fasted SGF), a compound of interest (e.g., a drug, e.g., a poorly soluble drug, e.g., VX-950) may dissolve, become supersaturated, and then crystallize. The polymer or plurality of polymers can prevent or decrease the crystallization of the compound in such or similar conditions, or during storage of a composition containing the compound. Stabilization can be measured, for example, by measuring the glass transition temperature of the solid dispersion, measuring the rate of relaxation of the amorphous material, or by measuring the solubility or bioavailability of the compound.

A polymer or plurality of polymers can be used in a formulation with a compound of interest (e.g., a drug, e.g., a poorly soluble drug, e.g., VX-950). One, more than one, or all of the polymers suitable for use in combination with the compound, for example to form a solid dispersion (e.g., agglomerated product) such as an amorphous solid dispersion, should have one or more of the following properties:

1. The glass transition temperature of the polymer or polymers in combination should have a temperature of no less than about 10-15° C. lower than the glass transition temperature of the compound. Preferably, the glass transition temperature of the polymer or polymers in combination is greater than the glass transition temperature of the compound, and in general at least 50° C. higher than the desired storage temperature of the drug product. For example, at least about 100° C., at least about 105° C., at least about 105° C., at least about 110° C., at least about 120° C., at least about 130° C., at least about 140° C., at least about 150° C., at least about 160° C., at least about 160° C., or greater.

2. The polymer or polymers in combination should be relatively non-hygroscopic. For example, the polymers should, when stored under standard conditions, absorb less than about 10% water, for example, less than about 9%, less than about 8%, less than about 7%, less than about 6%, or less than about 5%, less than about 4%, or less than about 3% water. Preferably the polymer or polymers will, when stored under standard conditions, be substantially free of absorbed water.

3. The polymer or polymers in combination should have similar or better solubility in solvents suitable for spray drying processes relative to that of the compound. In preferred embodiments, the polymer or polymers will dissolve in one or more of the same solvents or solvent systems as the compound. It is preferred that the polymer or polymers are soluble in at least one non-hydroxy containing solvent such as methylene chloride, acetone, or a combination thereof.

4. The polymer or polymers in combination, when combined with the compound, for example in a solid dispersion, should increase the solubility of the compound in aqueous and physiologically relative media either relative to the solubility of the compound in the absence of polymers or relative to the solubility of the compound when combined with a reference polymer. For example, the polymer or polymers could increase the solubility of amorphous compound by reducing the amount of amorphous compound that converts to crystalline compound from a solid amorphous dispersion.

5. The polymer or polymers in combination should decrease the relaxation rate of the amorphous substance.

6. The polymer or polymers in combination should increase the physical and/or chemical stability of the compound.

7. The polymer or polymers in combination should improve the manufacturability of the compound.

8. The polymer or polymers in combination should improve one or more of the handling, administration or storage properties of the compound.

9. The polymer or polymers in combination should not interact unfavorably with other pharmaceutical components, for example excipients.

The suitability of candidate polymer(s) (or other component) can be tested using the FSD methods described herein to form a composition containing an amorphous compound. The candidate composition can be compared in terms of stability, resistance to the formation of crystals, or other properties, and compared to a reference preparation, e.g., a preparation described herein, e.g., containing a compound of interest (e.g., a drug, e.g., a poorly soluble drug, e.g., VX-950). For example, a preparation of about 83% amorphous VX-950, about 17% HPMCAS, or crystalline VX-950. E.g., a candidate composition could be tested to determine whether it inhibits the time to onset of solvent mediated crystallization, or the percent conversion at a given time under controlled conditions, by at least 50%, 75%, 100%, or 110% as well as the reference preparation, or a candidate composition could be tested to determine if it has improved bioavailability or solubility of VX-950 relative to crystalline VX-950.

Surfactants

Products (e.g., agglomerated products such as powders or granules) being spray dried or undergoing fluidized spray drying, such as solid dispersions (e.g., amorphous solid dispersions) including a compound of interest (e.g., a drug, e.g., a poorly soluble drug, e.g., VX-950) and, optionally, a polymer or plurality of polymers (or solid state carrier(s)), may include a surfactant. A surfactant or surfactant mixture would generally decrease the interfacial tension between the solid dispersion and an aqueous medium. An appropriate surfactant or surfactant mixture may also enhance aqueous solubility and bioavailability of a compound of interest (e.g., a drug, e.g., a poorly soluble drug, e.g., VX-950) from a solid dispersion. The surfactants for use in connection with the present disclosure include, but are not limited to, sorbitan fatty acid esters (e.g., SPANS®), polyoxyethylene sorbitan fatty acid esters (e.g., TWEENS®), polysorbates, sodium lauryl sulfate (SLS, also known as SDS or sodium dodecyl sulfate), sodium dodecylbenzene sulfonate (SDBS) dioctyl sodium sulfosuccinate (Docusate), dioxycholic acid sodium salt (DOSS), Sorbitan Monostearate, Sorbitan Tristearate, hexadecyltrimethyl ammonium bromide (HTAB), Sodium N-lauroylsarcosine, Sodium Oleate, Sodium Myristate, Sodium Stearate, Sodium Palmitate, Gelucire 44/14, ethylenediamine tetraacetic acid (EDTA), vitamin E or tocol derivates, such as alpha tocopherol, (e.g., d-alpha tocopherol, dl-alpha tocopherol, tocopherol succinate esters) and tocopheryl esters, such as tocopheryl acetate esters, tocopheryl succinate esters, e.g., Vitamin E d-alpha tocopheryl polyethylene glycol 1000 succinate (TPGS; e.g., Vitamin E TPGS from Eastman), Lecithin, MW 677-692, Glutanic acid monosodium monohydrate, Labrasol, PEG 8 caprylic/capric glycerides, Transcutol, diethylene glycol monoethyl ether, Solutol HS-15, polyethylene glycol/hydroxystearate, Taurocholic Acid, Pluronic F68, Pluronic F108, and Pluronic F127 (or any other polyoxyethylene-polyoxypropylene co-polymers (PLURONICS®) or saturated polyglycolized glycerides (GELUCIRS®)). Specific example of such surfactants that may be used in connection with this disclosure include, but are not limited to, Span 65, Span 25, Tween 20, Capryol 90, Pluronic F108, sodium lauryl sulfate (SLS), Vitamin E TPGS, pluronics and copolymers, phospholipids such as PC (phosphatidylcholine) (e.g., from egg or soy), PIs (phosphatidylinositol), PAs (phosphatidic acid), PEs (phosphatidylethanolamine), PGs (phosphatidylglycerol). The surfactant could also be a lipid or fatty acid such as dipalmitoylphosphocholine (DPPC) or similar lipids (DAPC, DSPC, DPPG, etc.). Such lipids can be obtained synthetically, e.g., from Genzyme or Avanti Polar Lipids. SLS (e.g., Sigma or Fischer) and Vitamin E TPGS are preferred.

The amount of the surfactant (e.g., SLS or Vitamin E TPGS) relative to the total weight of the solid dispersion may be between about 0.1-20%. Preferably, it is from about 1% to about 20%, about 1 to about 15%, about 1 to about 10%, more preferably from about 1% to about 5%, e.g., about 1%, about 2%, about 3%, about 4%, or about 5%.

In certain embodiments, the amount of the surfactant relative to the total weight of the solid dispersion is at least about 0.1%, preferably at least about 0.5%, and more preferably at least about 1% (e.g., about 1%). In these embodiments, the surfactant would be present in an amount of no more than about 20%, and preferably no more than about 15%, about 12%, about 11%, about 10%, about 9%, about 8%, about 7%, about 6%, about 5%, about 4%, about 3%, about 2% or about 1%.

Candidate surfactants (or other components) and candidate amounts can be tested for suitability for use in the disclosure in a manner similar to that described for testing solvents.

Compositions/Packaging/Use

In one embodiment, the solid dispersion can be formulated into a pharmaceutical composition, e.g., a tablet. According to a preferred embodiment, the solid dispersion is present in an amount effective to have a therapeutic effect in a patient. Alternatively, a composition of this invention comprises another additional agent as described herein (e.g., to provide a combination therapy). Each component may be present in individual compositions, combination compositions, or in a single composition.

Pharmaceutical compositions, e.g., tablets, comprising the solid dispersion typically contain a pharmaceutically acceptable carrier, binder/diluent, surfactant, disintegrant, flow agent, lubricant, or vehicle (or carrier).

For example, a solid dispersion prepared as described herein can be directly compressed into a dosage form. In some embodiments, the dispersion is blended with one or more excipients prior to compression. As one example, a detailed description of direct compression of VX-950 is provided in the provisional application filed on Dec. 22, 2006, entitled DIRECTLY COMPRESSED DOSAGE FORMS, U.S. Provisional Application No. 60/871,712.

The compositions and processes of this invention may optionally include one or more excipients (see U.S. Pat. No. 6,720,003, U.S. Pub. App. No. 2004/0030151, and/or International Application WO 99/02542)). An excipient is a substance used as a carrier or vehicle in a dosage form, or added to a pharmaceutical composition, to improve handling, storage, or preparation of a dosage form. Excipients include, but are not limited to, diluents, disintegrants, adhesives, wetting agents, lubricants, glidants, crystallization inhibitors, surface modifying agents, agents to mask or counteract a disagreeable taste or odor, flavors, dyes, fragrances, fillers, binders, stabilizers and substances to improve the appearance of a composition.

As used herein, the term "comprising" is intended to be open-ended, thus indicating the potential inclusion of other agents in addition to the specified agents.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose based substances, polyethylene glycol, sodium carboxymethylcellulose, polyacrylates, waxes, polyethylene polyoxypropylene block polymers, polyethylene glycol and wool fat.

Pharmaceutical compositions, e.g., a solid dispersion, e.g., a spray dried drug, can be formulated into tablets. For example, a spray dispersion of a drug can be combined with a melt granulate, one or more diluents, and/or one or more disintegrants, and one or more lubricants, one or more other excipients, vehicles, carriers, and/or fillers, and compressed into a tableted form. The resulting tablet can then be further processed, for example, the tablet can be coated with a substance, such as a film or shellac, to help maintain the stability or integrity of the tablet, to facilitate the oral administration of the tablet, to mask the taste of the tablet, to add a flavor, to color the tablet, to regulate the release of the drug contained in the tablet once ingested and/or to mask the taste of the tableted formulation. Coatings suitable for this purpose (e.g., shellac, enteric coatings to regulate release) are known in the art. If desired, certain sweetening, flavoring, or coloring agents may also be added, to the tablet or to the coating. Techniques and compositions for making tablets are described, e.g., in *Remington's Pharmaceutical Sciences*, Arthur Osol, editor, pp. 1553-1593 (1980).

According to a preferred embodiment, the compositions of this invention are formulated for pharmaceutical administration to a mammal, preferably a human being. Although the forms of tablets provided herein are preferably formulated for oral administration, other formulations could be obtained.

The invention also provides pharmaceutical packs and kits comprising a tableted formulation of amorphous VX-950, or a pharmaceutical composition according to any of the embodiments herein.

Pharmaceutical compositions, e.g., containing a solid (e.g., spray dried) dispersion described herein, may also be prescribed to the patient in "patient packs" containing more than one dose, and preferably the whole course of treatment, in a single package, (e.g., a blister pack). Patient packs have an advantage over traditional prescriptions, where a pharmacist divides a patients supply of a pharmaceutical from a bulk supply, in that the patient always has access to the package insert contained in the patient pack, which is normally missing in traditional prescriptions. The inclusion of a package insert has been shown to improve patient compliance with the physician's instructions. Preferably the drug is in an oral dosage, e.g., tablet, form.

It will be understood that the administration of the combination of the invention by means of a single patient pack, or patient packs of each formulation, containing within a package insert instructing the patient to the correct use of the disclosure is a desirable additional feature of this disclosure.

In an alternative embodiment of this disclosure, the pharmaceutical pack further comprises one or more of additional agents as described herein. The additional agent or agents may be provided in the same pack or in separate packs.

According to a further aspect of the disclosure is a pack comprising at least any tableted form of the solid (e.g., spray dried) dispersion or any composition according to this disclosure, and an information insert containing directions on the use of the composition of the disclosure (or the use of a combination of the composition of this disclosure and an additional agent or agents described herein).

Accordingly, this disclosure provides kits for the simultaneous or sequential administration of solid (e.g., spray dried) dispersion or any composition according to this disclosure (and optionally an additional agent) or derivatives thereof that are prepared in a conventional manner. Typically, such a kit will comprise, e.g., a composition of each inhibitor and optionally the additional agent(s) in a pharmaceutically acceptable carrier (and in one or in a plurality of pharmaceutical formulations) and written instructions for the simultaneous or sequential administration. Preferably the drug is in an oral dosage, e.g., tablet, form.

In another embodiment, a packaged kit is provided that contains one or more dosage forms (preferably an oral dosage form) for self administration; a container means, preferably sealed, for housing the dosage forms during storage and prior to use; and instructions for a patient to carry out drug administration. The instructions will typically be written instructions on a package insert, a label, and/or on other components of the kit, and the dosage form or forms are as described herein. Each dosage form may be individually housed, as in a sheet of a metal foil-plastic laminate with each dosage form isolated from the others in individual cells or bubbles, or the dosage forms may be housed in a single container, as in a plastic bottle or a vial. The present kits will also typically include means for packaging the individual kit components, i.e., the dosage forms, the container means, and the written instructions for use. Such packaging means may take the form of a cardboard or paper box, a plastic or foil pouch, etc.

Embodiments of this disclosure may also involve additional agents. Therefore, a method of this disclosure may involve steps as administering such additional agents.

Dosage

Dosage levels of from about 0.01 to about 100 mg/kg body weight per day, preferably from about 10 to about 100 mg/kg body weight per day of solid (e.g., spray dried) dispersion are useful for the prevention and treatment of the condition for which the subject is being treated. In some embodiments, dosage levels are from about 0.4 to about 10 g/day, for example from about 1 to about 4 g/day, preferably from about 2 to about 3.5 g/day, per person (based on the average size of a person calculated at about 70 kg) are included. Typically, the pharmaceutical compositions of, and according to, this disclosure will be administered from about 1 to about 5 times per day, preferably from about 1 to about 3 times per day, or alternatively, as a continuous infusion. In some embodiments, solid (e.g., spray dried) dispersion or pharmaceutical composition comprising it is administered using a controlled release formulation. In some embodiments, this can help to provide relatively stable blood levels of the solid (e.g., spray dried) dispersion.

In some embodiments, the dose of the solid (e.g., spray dried) dispersion can be a standard dose, e.g., about 1 g to about 5 g a day, more preferably about 2 g to about 4 g a day, more preferably about 2 g to about 3 g a day, e.g., about 2.25 g or about 2.5 g a day. The dose can be administered e.g., as a spray dried dispersion or as a tablet.

Such administration can be used as a chronic or acute therapy. The amount of active ingredient that may be combined with the carrier materials to produce a single dosage form will vary depending upon the subject treated and the particular mode of administration. A typical preparation will contain from about 5% to about 95% active compound (w/w). Preferably, such preparations contain from about 20% to about 80%, from about 25% to about 70%, from about 30% to about 60% active compound.

When the compositions or methods of this disclosure involve a combination of the solid (e.g., spray dried) dispersion and one or more additional therapeutic or prophylactic agents, both the solid (e.g., spray dried) dispersion and the additional agent should be present at dosage levels of between about 10 to 100%, and more preferably between about 10 to 80% of the dosage normally administered in a monotherapy regimen.

Upon improvement of a patient's condition, a maintenance dose of a compound, composition or combination of this disclosure may be administered, if necessary. Subsequently, the dosage or frequency of administration, or both, may be reduced, e.g., to about ½ or ¼ or less of the dosage or frequency of administration, as a function of the symptoms, to a level at which the improved condition is retained when the symptoms have been alleviated to the desired level, treatment should cease. Patients may, however, require intermittent treatment on a long-term basis upon any recurrence of disease symptoms.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular described compound and the presence or absence and the nature of the additional anti-viral agent in the composition.

EXAMPLES

Example 1

A mixture of the following components was spray dried to provide a solid dispersion of VX-950. VX-950HPMCAS- HG/SLS was combined in a ratio of 49.5/49.5/1 wt/wt and combined in a solvent system at a solid concentration of 10, where the solvent system included methylene chloride/acetone/glacial acetic acid in a ratio of 66.6/28.5/5 to provide a product having a d50 of 43.03 and a bulk density of 0.37.

Example 2

A mixture of the following components was spray dried to provide a solid dispersion of VX-950. VX-950/HPMCAS-HG/SLS was combined in a ratio of 49.5/49.5/1 wt/wt and combined in a solvent system at a solid concentration of 10, where the solvent system included methylene chloride/acetone/glacial acetic acid in a ratio of 63/27/10 to provide a product having a d50 of 47.02 and a bulk density of 0.41.

Example 3

Spray dried dispersions of VX-950 were prepared using with multiple VX-950 lots, HPMCAS-HG (Hypromellose Acetate Succinate, HG grade, Shin-Etsu Chemical Co.) polymer, and SLS (Sodium Lauryl Sulfate, Fisher) surfactant. Spray drying and subsequent post-drying in a biconical dryer were performed. Dry dispersion with low residual solvent levels and target powder properties were manufactured. Success criteria included having acceptable process yield (>80%), and meeting all target drug product specifications for purity, and matching the target properties within the range specified for physical characteristics (particle size and bulk density).

Formulation Composition and Process Outline

The overall formulation composition for each of two active dispersion manufactures is described in Table 1.

TABLE 1

Formulation composition of each of the two active dispersion manufactures based off of 116.25 kg VX-950 at 13 wt %.

| Component Function | Component | kg |
| --- | --- | --- |
| API | VX-950 | 116.25 |
| Polymer/Dispersant | Hypromellose Acetate Succinate, NF/JPE (HPMCAS-HG) | 116.25 |
| Surfactant | Sodium Lauryl Sulfate, NF (SLS) | 2.348 |
| Process Solvent | Methylene Chloride, NF (for Dispersion) | 1178.8 |
| Process Solvent | Acetone, NF (for Dispersion) | 377.2 |
| Process Solvent | DI Water | 15.7 |

A flowchart schematic of a manufacturing process is given in FIG. 1.

An explanation of the process flow is below:

A) Preparation of Solution and Spray Dryer

1) Methylene chloride was prepared in the equilibration solvent tank.

2) 100 kg of the prescribed acetone amount was added to the mixing reactor (refer to Table 1).

3) Methylene chloride at the appropriate amount (refer to Table 1) was prepared in the main solution reactor. Differential pressure cells confirmed the correct amounts of charged solvents.

4) VX-950 drug substance was charged into the main solution reactor (refer to Table 1). The overall solids loading was at 13 wt %. A sample was taken to verify the drug substance was dissolved by visual inspection.

5) HPMCAS-HG was charged into the main solution reactor (refer to Table 1). The overall solids loading were at 13 wt %.

6) The remaining prescribed acetone amount was added to the mixing reactor (refer to Table 1).

7) The acetone, SLS, and DI water were charged into the main solution reactor.

8) The resultant batch was tested for visual appearance and viscosity once dissolved.

9) The Spraying Systems SK-MFP pressure nozzle was installed and tested for correct atomization with the equilibration solvent. (Nozzles 48/21, 50/21, or 52/21 can also be used.)

B) Start-up of the Spray Dryer

1) The spray dryer was heated to the appropriate outlet temperature.

2) Equilibration solvents were sprayed until all parameters are equilibrated and constant.

3) Spray drying of the feed solution was commenced once the spray dryer was equilibrated.

4) Dry particles were inertially separated from the process gas by a cyclone and collected within polyethylene bags. The process gas was then filtered for fine particles and condensed to remove process solvents.

5) Initial sample was taken and tested for particle size distribution and bulk and tap densities.

a) If particle size distribution and densities were within acceptance criteria and near targets (refer to Table 6), the process continued and samples were taken per the sampling plan.

b) If particle size distribution and densities were not within acceptance criteria and not near targets (refer to Table 6), the process was optimized (e.g., by changing one or more of the following: nozzle, outlet temperature, feed pressure) as needed. Collection bags were changed and the powder outside of the acceptance criteria was held in quarantine. Once the sample was within specification, the process with current parameters was started.

C) On-going Spray Drying

1) Took samples per sampling plan.

2) Noted any changes to the processing parameters.

3) Noted any stoppages or out of continuous operation occurrences.

4) Upon completion of spray drying the feed solution, switched to equilibration solvent and followed normal shut down procedures.

D) Post-Drying Process

1) Spray dried dispersion was charged into a secondary dryer and dried until all residual solvents (methylene chloride, acetone, ethyl acetate, and toluene) were below the specifications established.

Equipment

An 8000-L industrial scale reactor equipped with a mechanical stirrer and thermal circuit was used for mixing of the initial solution. An industrial scale spray dryer (Niro Pharmaceutical Spray Dryer FSD12.5CC) was used in normal co-current spray drying mode. A pressure nozzle system (Spraying Systems Maximum Free Passage SK-MFP Series variety, orifice 48-54, core 21) was utilized. A high performance pressure pump with solvent-compatible/resistant gaskets pumped the feed solution through the atomizer into the spray drying vessel. An inertial cyclone separated the product from the process gas and solvent vapors. A filter bag then collected the fine particles not separated by the cyclone. The resultant gas was condensed to remove process solvents and recycled back to the heater and spray dryer (closed cycle).

Figure 2:
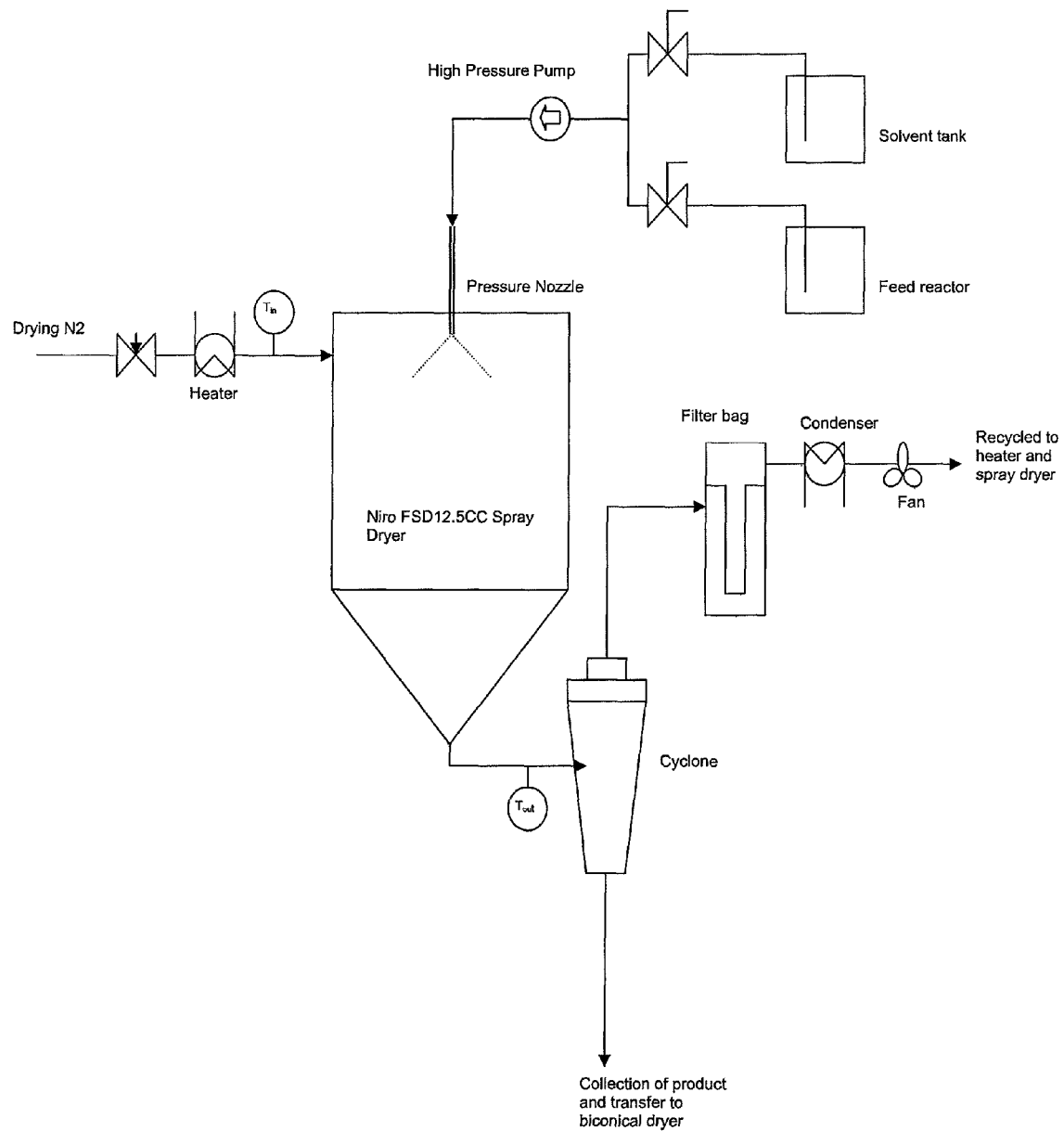
FIG. 2 is a schematic of a spray drying process.

FIG. 2 was a schematic of the spray drying process.

The resultant product was transferred to a biconical vacuum dryer for drying of residual solvents.

Key Process Controls and Parameters

Key process controls and parameters were needed for both the spray drying and biconical drying process. The primary process controls parameters have been identified through preliminary research batches.

Key process controls and parameters for the spray drying process, which were monitored and recorded over the entirety of the run time, were:

Atomizer/nozzle Installed
Feed Pressure
Inlet Temperature
Condenser Temperature Set Point (at about −10 to −15° C.)

Key process metrics for the spray drying process, which were monitored and recorded over the entirety of the run time, were:

Solution Feed Rate
Outlet Temperature
Cyclone Pressure Differential and Drying Gas Flow Rate Table 2 defines spray drying process parameters/metrics, settings/ranges, and target guidelines.

TABLE 2

Spray drying variables, settings, and targets

| Variable | Setting/Range |
| --- | --- |
| Atomizer Installed | Spray Systems SK-MFP |
| Solution Feedrate | 120-200 kg/hr |
| Feed Pressure | 20-50 bar |
| Inlet Temperature | 50-80° C. |
| Outlet Temperature | 25-31° C. |
| Cyclone Pressure Differential | 10.5-13.5 cm $H_2O$ |

Materials

All excipients and process solvents used complied with the current monographs of the European Pharmacopoeia, the Japanese Pharmacopoeia or the USP/NF, as indicated in Tables 1 and 3. All excipients and process solvents were purchased from approved suppliers. Manufacturer certificates of analysis were accepted and all materials received will undergo testing.

TABLE 3

Materials

| Material | Source |
| --- | --- |
| VX-950 | |
| Hypromellose Acetate Succinate, NF/JPE (HPMCAS) (Aqoat AS-HG) | Shin-Etsu Chemical Co. |
| Sodium Lauryl Sulfate (SLS), NF | Sigma/Fisher |
| Methylene Chloride, NF | |
| Acetone, NF | |
| DI Water | |

Variations in Manufacture

Manufacture 2 used a process optimized for dispersion. Most notably this dispersion had larger particle size and bulk density than Manufacture 1, as needed for enhanced powder flowability and direct compression on a high-speed tablet press. Spray drying parameters were varied to make such powder. Variations were also made to tighten the process and to avoid possible deviations.

Example 4

Spray dried dispersions of VX-950 were prepared using a solvent system that contained water, as described. The solvent system contained 75% methylene chloride; 24% acetone; and 1% water (w/w/w). The dispersions contained 49.5% VX-950; 49.5% HPMCAS-HG; and 1% SLS (w/w/w). As indicated in FIG. 3, various combinations of outlet temperature, feed pressure, cyclone pressure, condenser setpoint temperature, nozzle type, solids loading, and solution feedrate were tested in the spray drying process. As indicated in FIG. 3, varying these parameters varied the properties (particle size (PS)), span, bulk density, tap density, and levels of residual solvents) of the resulting dispersions.

Example 5

Objectives and Success Criteria

Dry dispersion with low residual solvent levels and target powder properties are manufactured. Success criteria include having acceptable process yield (>80%), and meeting all target drug product specifications for purity, and matching the target properties within the range specified for physical characteristics (particle size and bulk density).

Formulation Composition and Process Outline

The overall formulation composition for the two active dispersion manufactures is described in Table 4.

TABLE 4

Formulation composition of the first active dispersion manufacture based off of 100 kg VX-950 at 15 wt %.

| Component Function | Component | kg |
| --- | --- | --- |
| API | VX-950 | 200.0 |
| Polymer/Dispersant | Hypromellose Acetate Succinate, NF/JPE (HPMCAS-HG) | 100.0 |
| Surfactant | Sodium Lauryl Sulfate, NF (SLS) | 2.02 |
| Process Solvent | Methylene Chloride, NF (for Dispersion) | 858.6 |
| Process Solvent | Acetone, NF (for Dispersion) | 274.7 |
| Process Solvent | DI Water | 11.4 |

Figure 4:
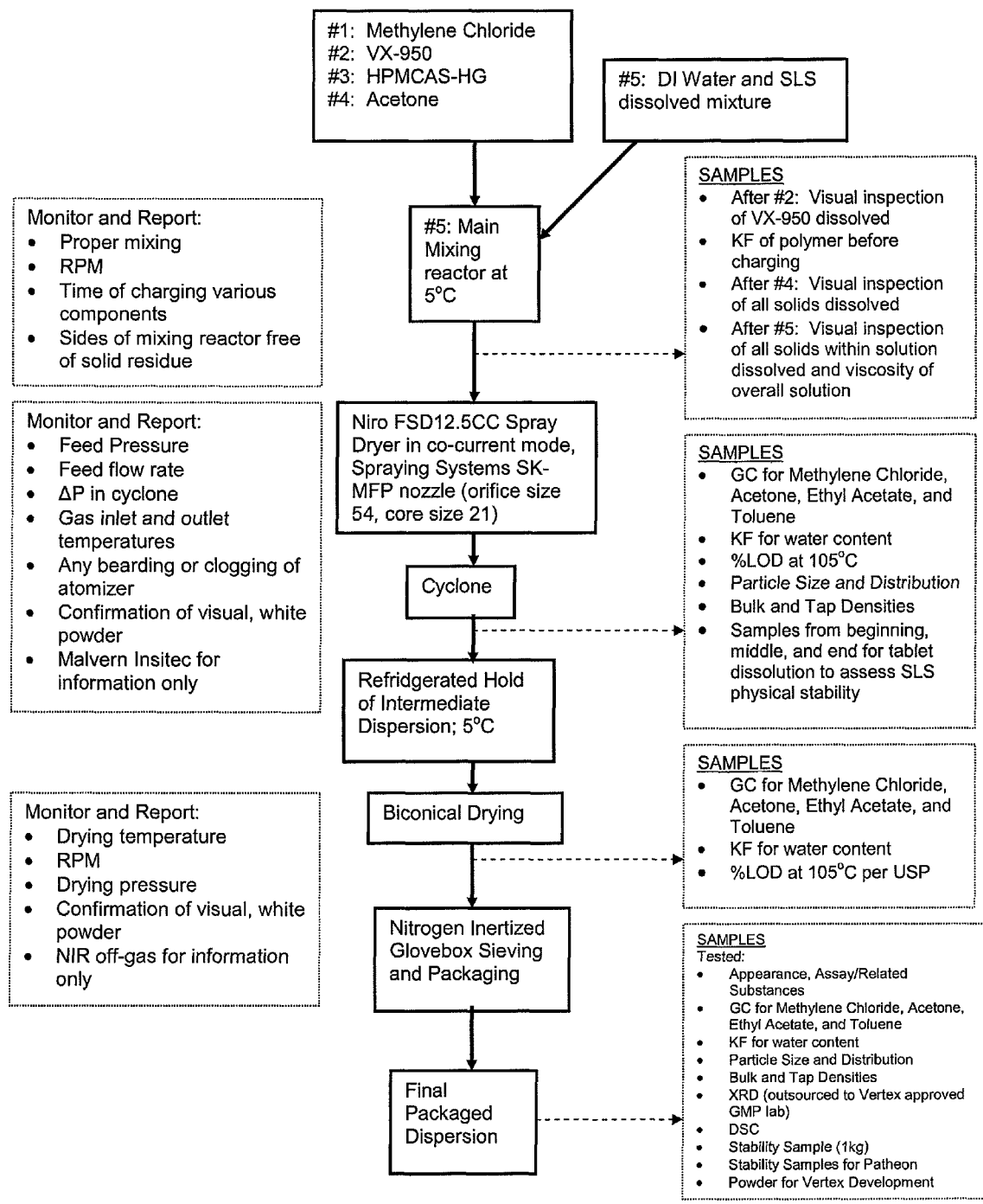
FIG. 4 is a flowchart of manufacturing process, control, sampling, and testing.

A flowchart schematic of the manufacturing process is given in FIG. 4.

An explanation of the process flow is below:

A) Preparation of Solution and Spray Dryer

1) Methylene chloride is prepared in the equilibration solvent tank.
2) DI water is charged into a secondary mixing vessel (refer to Table 4).
3) Methylene chloride at the appropriate amount (refer to Table 4) is prepared in the main solution reactor. Differential pressure cells confirm the correct amounts of charged solvents.
4) VX-950 drug substance is charged into the main solution reactor (refer to Table 7). The overall solids loading are at 15 wt %. A sample is taken to verify the drug substance is dissolved by visual inspection.
5) HPMCAS-HG is charged into the main solution reactor (refer to Table 4). The overall solids loading is at 15 wt %.
6) The acetone amount is added to the mixing reactor (refer to Table 4). A sample is taken to determine if all solids are dissolved.

7) The SLS and water are added to the main mixing reactor.
8) The Spraying Systems SK-MFP pressure nozzle is installed and tested for correct atomization with the equilibration solvent.

B) Start-up of the Spray Dryer
1) The spray dryer is heated to the appropriate outlet temperature.
2) Equilibration solvents are sprayed until all parameters are equilibrated and constant.
3) Spray drying of the feed solution is commenced once the spray dryer is equilibrated.
4) Dry particles are inertially separated from the process gas by a cyclone and collected within polyethylene bags. The process gas is then filtered for fine particles and condensed to remove process solvents.
5) Initial sample is taken and tested for particle size distribution and bulk and tap densities.
   a) If particle size distribution and densities are within acceptance criteria and near targets (refer to Table 11), the process continues and samples are taken per the sampling plan.
   b) If particle size distribution and densities are not within acceptance criteria and not near targets (refer to Table 11), the process is optimized (by changing one or more of the following: outlet temperature, feed pressure, or condenser temperature as needed. Collection bags are changed and the powder outside of the acceptance criteria is held in quarantine. Once the sample is within specification, start the process with current parameters.

C) Post-Drying Process
1) Spray dried dispersion is charged into a secondary dryer.
2) This continues until all residual solvents (methylene chloride, acetone, ethyl acetate, and toluene) are below the specifications established.

D) Testing, Shipment
1) Samples of this dispersion are tested for release testing.

Equipment

An 8000-L industrial scale reactor (R240) equipped with a mechanical stirrer and thermal circuit is used for mixing of the initial solution. A reactor (R32) is used for the SLS and water mixture. An industrial scale spray dryer (Niro Pharmaceutical Spray Dryer FSD12.5CC) is used in normal co-current spray drying mode. A pressure nozzle system (Spraying Systems Maximum Free Passage SK-MFP Series variety, orifice 54, core 21) is utilized. A high performance pressure pump with solvent-compatible/resistant gaskets pumps the feed solution through the atomizer into the spray drying vessel. An inertial cyclone separates the product from the process gas and solvent vapors. A filter bag then collects the fine particles not separated by the cyclone. The resultant gas is condensed to remove process solvents and recycled back to the heater and spray dryer (closed cycle).

FIG. 2 is a schematic of the spray drying process.

The resultant product is transferred to a biconical vacuum dryer (S901) for drying of residual solvents. The dry product is sieved within a nitrogen swept glovebox and packaged.

Key Process Controls and Parameters

Key process controls and parameters are needed for both the spray drying and biconical drying process. The primary process controls parameters have been identified through preliminary research batches.

Key process controls and parameters for the spray drying process, which need to be monitored and recorded over the entirety of the run time, are:
Atomizer/nozzle Installed
Feed Pressure
Inlet Temperature
Condenser Temperature Set Point Key process metrics for the spray drying process, which need to be monitored and recorded over the entirety of the run time, are:
Solution Feed Rate
Outlet Temperature
Cyclone Pressure Differential and Drying Gas Flow Rate Table 5 defines spray drying process parameters/metrics, settings/ranges, and target guidelines.

TABLE 5

Spray drying variables, settings, and targets

| Variable | Setting/Range |
| --- | --- |
| Atomizer Installed | Spray Systems SK-MFP |
| Solution Feedrate | 130-180 kg/hr |
| Feed Pressure | 40-65 bar |
| Outlet Temperature | 22-29° C. |
| Cyclone Pressure Differential | 10.0-12.5 cm $H_2O$ |

Materials

All excipients and process solvents used comply with the current monographs of the European Pharmacopoeia, the Japanese Pharmacopoeia or the USP/NF as indicated in Tables 4 and 6. All excipients and process solvents are purchased from approved suppliers. Manufacturer certificate of analysis are accepted and all materials received undergo testing.

TABLE 6

| Materials |
| --- |
| Material |
| VX-950 |
| Hypromellose Acetate Succinate, NF/JPE (HPMCAS) (Aqoat AS-HG) |
| Sodium Lauryl Sulfate (SLS), NF |
| Methylene Chloride, NF |
| Acetone, NF |
| DI Water |

Variations in Manufacture

The manufactures utilize a 10% or 30 wt % solution. Also, the solution manufacture can be varied. In some batches, the SLS/DI Water mixture is added last to the main solution reactor. Inlet temperature of the spray dryer is monitored but in some manufactures a range or a target is not defined. Reduced in-process sampling is instructed. KF testing on the polymer prior to charging can be performed.

A number of embodiments of the invention have been described. Nevertheless, it will be understood that various modifications may be made without departing from the spirit and scope of the disclosure. Accordingly, other embodiments are within the scope of the following claims.

What is claimed is:

1. A method of spray drying the drug VX-950, the method comprising forming or providing a mixture of the drug in a solvent system that comprises at least a volatile solvent and a non-volatile solvent, the non-volatile solvent in an amount of from about 0.1% to about 20% by wt of said solvent system to form a mixture of the drug and the solvent system, and spray-drying the mixture to obtain amorphous drug product, wherein the solvent system comprises methylene chloride, acetone, and water.

2. The method of claim 1, wherein the mixture comprises a solution or a suspension.

3. The method of claim 1, wherein the non-volatile solvent comprises water.

4. The method of claim 1, wherein the solvent system comprises from about 40% to about 80% methylene chloride, from about 20% to about 35% acetone, and from about 0.1% to about 15% water.

5. The method of claim 1, wherein the mixture comprises a surfactant.

6. The method of claim 5, wherein the surfactant comprises sodium lauryl sulfate.

7. The method of claim 1, wherein the amorphous VX-950 drug product has a chemical stability represented by retention of about 95% amorphous VX-950 in said drug product when stored at 25° C. in a closed water tight container.

* * * * *

UNITED STATES PATENT AND TRADEMARK OFFICE
CERTIFICATE OF CORRECTION

| | | |
|---|---|---|
| PATENT NO. | : 8,853,152 B2 | Page 1 of 1 |
| APPLICATION NO. | : 12/481962 | |
| DATED | : October 7, 2014 | |
| INVENTOR(S) | : Kevin Bittorf et al. | |

It is certified that error appears in the above-identified patent and that said Letters Patent is hereby corrected as shown below:

On the title page, item (75) please replace
"Jeffrey Kastra" with
"Jeffrey Katstra"

Signed and Sealed this
Sixth Day of January, 2015

Michelle K. Lee
*Deputy Director of the United States Patent and Trademark Office*